United States Patent
Yu et al.

(10) Patent No.: US 10,676,537 B2
(45) Date of Patent: Jun. 9, 2020

(54) ANTIBODY TARGETED TO TISSUE FACTOR, PREPARATION METHOD THEREFOR, AND USE THEREOF

(71) Applicants: FUDAN UNIVERSITY, Shanghai (CN); SHANGHAI MIRACOGEN INC., Shanghai (CN)

(72) Inventors: Ke Yu, Shanghai (CN); Xuesai Zhang, Shanghai (CN); Qing Lin, Shanghai (CN); Qingrou Li, Shanghai (CN)

(73) Assignees: Fudan University, Shanghai (CN); Shanghai Miracogen Inc., Shanghai (CN)

( * ) Notice: Subject to any disclaimer, the term of this patent is extended or adjusted under 35 U.S.C. 154(b) by 0 days.

(21) Appl. No.: 16/326,881

(22) PCT Filed: Feb. 20, 2017

(86) PCT No.: PCT/CN2017/074163
§ 371 (c)(1),
(2) Date: Feb. 20, 2019

(87) PCT Pub. No.: WO2018/036117
PCT Pub. Date: Mar. 1, 2018

(65) Prior Publication Data
US 2019/0177431 A1   Jun. 13, 2019

(30) Foreign Application Priority Data

Aug. 22, 2016 (CN) .......................... 2016 1 0705557

(51) Int. Cl.
| | | |
|---|---|---|
| *C07K 16/36* | (2006.01) |
| *A61K 47/68* | (2017.01) |
| *A61P 7/02* | (2006.01) |
| *A61P 3/00* | (2006.01) |
| *A61P 29/00* | (2006.01) |
| *A61P 35/00* | (2006.01) |
| *C07K 16/06* | (2006.01) |
| *C12N 15/85* | (2006.01) |
| *G01N 33/86* | (2006.01) |
| *A61K 39/00* | (2006.01) |

(52) U.S. Cl.
CPC .......... *C07K 16/36* (2013.01); *A61K 47/6803* (2017.08); *A61K 47/6843* (2017.08); *A61P 3/00* (2018.01); *A61P 7/02* (2018.01); *A61P 29/00* (2018.01); *A61P 35/00* (2018.01); *C07K 16/065* (2013.01); *C12N 15/85* (2013.01); *G01N 33/86* (2013.01); *A61K 2039/505* (2013.01); *C07K 2317/24* (2013.01); *C07K 2317/76* (2013.01); *C07K 2317/77* (2013.01); *C07K 2317/92* (2013.01); *G01N 2333/7454* (2013.01)

(58) Field of Classification Search
None
See application file for complete search history.

(56) References Cited

U.S. PATENT DOCUMENTS

| | | | | |
|---|---|---|---|---|
| 6,274,142 B1* | 8/2001 | O'Brien | ............... | A61K 39/395 424/130.1 |
| 7,579,000 B2* | 8/2009 | Light | ............... | C07K 16/36 424/133.1 |
| 7,605,235 B2* | 10/2009 | Anderson | ............... | C07K 16/36 424/178.1 |
| 7,749,498 B2* | 7/2010 | Jiao | ............... | A61K 39/395 424/130.1 |
| 7,968,094 B2* | 6/2011 | Jiao | ............... | C07K 16/36 424/133.1 |
| 2014/0079628 A1* | 3/2014 | Anderson | .......... | A61K 47/6849 424/1.11 |
| 2014/0234304 A1 | 8/2014 | Almagro et al. | | |
| 2016/0053020 A1 | 2/2016 | Verploegen et al. | | |

FOREIGN PATENT DOCUMENTS

| | | | |
|---|---|---|---|
| CN | 1575302 A | 2/2005 | |
| CN | 102317319 A | 1/2012 | |
| CN | 103119065 A | 5/2013 | |
| CN | 104387474 A | 3/2015 | |
| CN | 103342752 A | 10/2019 | |
| WO | WO-9405328 A1 * | 3/1994 | ............ C07K 14/745 |
| WO | 03/029295 A1 | 4/2003 | |
| WO | WO-2007056352 A2 * | 5/2007 | ............ C07K 16/36 |
| WO | 2008/137382 A1 | 11/2008 | |
| WO | 2011/157741 A2 | 12/2011 | |
| WO | 2015/115656 A1 | 8/2015 | |
| WO | WO-2017028823 A1 * | 2/2017 | ............ C07K 16/36 |

OTHER PUBLICATIONS

International Search Report for Application No. PCT/CN2017/074163, dated May 25, 2017. (English Translation).
Qu, Xuefeng et al., "Molecular Mechanism of Tissue Factor in Cardiovascular Disease and Significance Thereof," Chinese Circulation Journal, p. 480, non-official translation, Dec. 31, 2007.
Office Action, Chinese Application No. 201610705557.4, dated Mar. 28, 2019.
Supplementary European Search Report corresponding to European Application No. EP 17 84 2543.5, 9 pages, dated Mar. 11, 2020.

* cited by examiner

*Primary Examiner* — Michael Szperka
(74) *Attorney, Agent, or Firm* — Seed IP Law Group LLP

(57) ABSTRACT

The present invention provides a tissue factor (TF) monoclonal antibody and a preparation method therefor. The monoclonal antibody provided by the present invention can specifically bind with a TF antigen, has high affinity and low immunogenicity, and has the activity of resisting tumors and the like.

17 Claims, 14 Drawing Sheets
Specification includes a Sequence Listing.

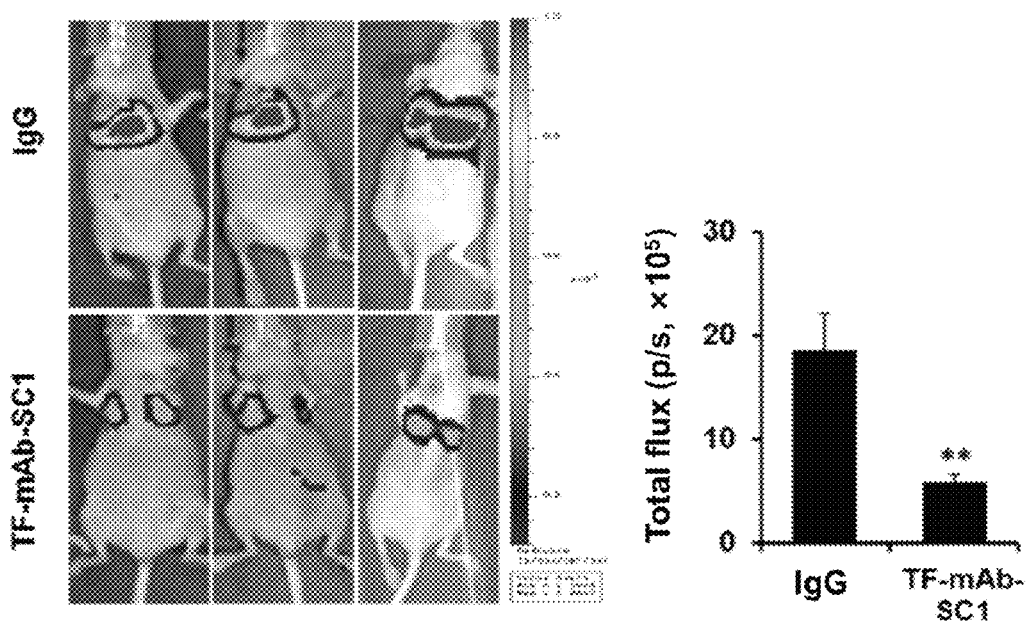
Fig. 17
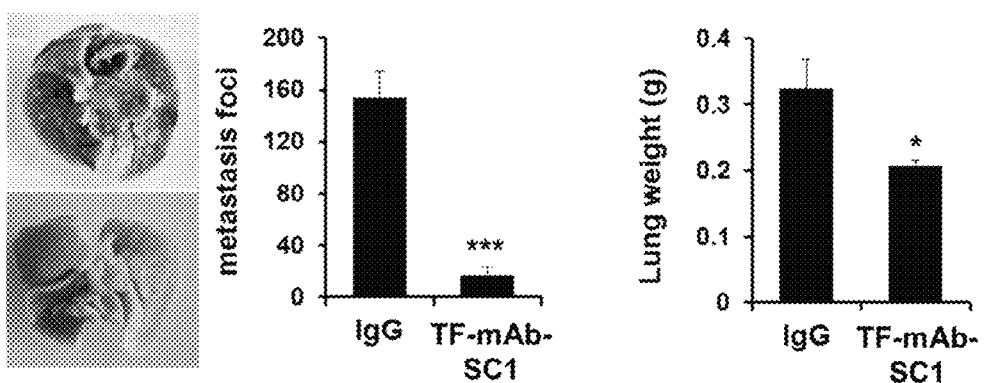
Fig. 18A
Fig. 18B
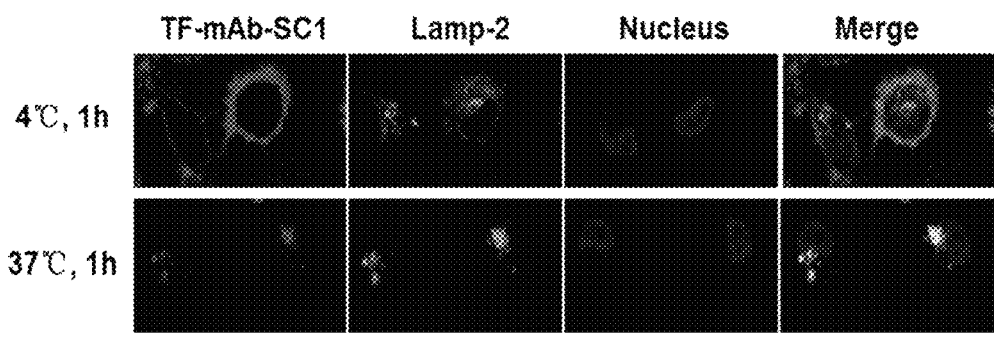
Fig. 19

ANTIBODY TARGETED TO TISSUE FACTOR, PREPARATION METHOD THEREFOR, AND USE THEREOF

INCORPORATION BY REFERENCE OF MATERIAL SUBMITTED ELECTRONICALLY

This application contains, as a separate part of disclosure, a sequence listing in computer-readable form (filename: 53910_Seqlisting.txt; Size: 14,540 bytes; Created: Feb. 18, 2019) which is incorporated by reference in its entirety.

TECHNICAL FIELD

The present invention relates to an antibody, particularly an antibody targeted to human tissue factor (TF), a preparation method and use thereof.

BACKGROUND ART

Tissue factor (TF) is a 47 kDa transmembrane glycoprotein. Under normal physiological conditions, TF expression is mainly restricted to the cells in subendothelial layer; once the blood vessels are damaged in an organism, TF will be exposed to the blood stream, and initiates extrinsic coagulation reaction by binding to and activating factor VII.

It has been found in studies that TF is abnormally activated and expressed in many tumor tissues, and plays an important role in the development and progression of tumors. Especially in the advanced stage of cancer, most patients are accompanied by spontaneous thrombosis, such as Deep-vein thrombosis (DVT), Disseminated intravascular coagulation (DIC) and Pulmonary embolism (PE) (Thrombosis research, 2013, 131: S59-S62; Journal of Thrombosis and Haemostasis, 2011, 9(s1): 306-315); the abnormal expression of TF in tumor cells is the main cause responsible for these symptoms. Analysis on clinical samples of many tumors shows that the expression level of TF directly affects the deterioration indexes such as metastasis of tumor and occurrence of thrombosis in patients, for example, the percentage of abnormal TF expression was 85.8% in breast cancer, 88.5% in pancreatic cancer, 83.6% in lung cancer, and 91.3% in esophageal cancer, etc. (Blood, 2012, 119: 924-932).

In addition to the initiation of the extrinsic coagulation reaction, a TF/FVIIa complex can directly bind to and induce the activation of a transmembrane G protein-coupled receptor, protease-activated receptor 2 (PAR2). PAR2 is an important signal pathway that regulates inflammatory response. Although there are few studies on PAR2 in the field of tumors, it is conceivable that TF can affect a series of tumor function signals in cells by virtue of PAR2. In summary, TF-PAR2 induces the gene expression of key growth factors, immunoregulators, and chemokines (e.g. VEGF, CSF1/2, IL8, CXCL1, etc.), promotes neovascularization, and provides adequate nutrients, energy and a suitable microenvironment for tumor growth by MAPK/ERK phosphorylation. In addition, TF can also enhance the migration and adhesion of tumor cells by interaction with Rac 1 and β1 family-related integrin, so as to enhance the hematogenous metastatic ability of tumor cells in general (Journal of Thrombosis research, 2012, 130: S84-S87; Journal of Thrombosis and Haemostasis, 2013, 11: 285-293; International Journal of Cancer, 2014, doi: 10.1002/ijc.28959; Blood, 2012, 119: 924-932).

Meanwhile, TF-induced hypercoagulative state directly promotes survival and hematogenous metastasis of tumor cells (Blood, 2008, 111: 190-9; Cancer Res., 2015, 75 (1 Suppl): Abstract nr B19), i.e. the TF/FVIIa-initiated coagulation results in the formation of thrombin and the deposition of fibrin, which not only enables tumor cells to escape from immune attack, but also enhances the interaction between tumor cells and endothelial cells, which helps the diffusion and infiltration of tumor cells, and facilitates the occurrence of hematogenous metastasis. This is also an important reason why it is difficult to treat cancer now.

Studies have shown that TF also plays a role in thrombotic diseases. In addition to its role in the development and progression of tumor, TF or MPTF (Microparticle tissue factor)-initiated coagulation is also an important reason for triggering Venous thromboembolism (VTE), and moreover, its content in blood is directly proportional to the severity degree of VTE. Now, there are many studies showing that TF can be used as an important marker for diagnosis and assessment of the condition in VTE patients in clinic, and as a potential target for VTE treatment (Thrombosis research, 2010, 125: 511-512; Lupus., 2010, 19: 370-378; Annual review of physiology, 2011, 73: 515-525). The role of TF in arterial thrombotic diseases can not be ignored, either. A lot of clinical data indicates that TF plays an important role in the development and progression of atherosclerosis. In 2009, Steppich B A, Braun SL et al. conducted research in 174 patients with unstable Angina Pectoris (uAP) and 112 patients with Acute myocardial infarction (AMI), and the results showed that the activity of TF in plasma had a direct effect on the mortality of patients with cardiovascular disease, and TF could be used as a marker for diagnosis and prognosis of cardiovascular disease (Thrombosis research, 2012, 129: 279-284; Thromb J., 2009, 7(11): 1-9); in 2014, Jiang P, Xue D et al. conducted research to the photochemically induced thrombosis model and the $FeCl_3$-induced thrombosis model, and showed that as compared with the intrinsic pathway of blood coagulation, the TF-initiated extrinsic pathway of blood coagulation played a more important role in the development and progression of arterial thrombotic diseases, and the experimental results further proved the TF-initiated extrinsic pathway of blood coagulation could be used as a target for the treatment of arterial thrombotic diseases (Thrombosis research, 2014, 133(4): 657-666).

TF also plays a role in inflammation and metabolic diseases. Studies have shown that the development of an inflammatory disease is accompanied by abnormal angiogenesis and coagulation. The studies conducted by Maria I Bokarewa et al. have shown that a variety of inflammatory stimuli promoted the expression of TF on the surface of endothelial cells and mononuclear cells, and their experimental results showed that overexpression of TF was also a major factor for inducing and promoting inflammation (Arthritis Res 2002, 4:190-195).

Moreover, studies have also shown that TF plays a significant regulatory role in the treatment of obesity and diabetes. For example, the studies conducted by Leylla Badeanlou et al. have shown that the blockage of TF-PAR2 signal pathway by specific antibodies targeted to TF or knocking out TF could significantly inhibit the development of diet-induced obesity and adipose tissue inflammation, and can significantly improve the therapeutic effect of insulin on diabetes (Nature medicine, 2011, 17(11): 1490-1497).

Therefore, in view of the roles and functions of TF in various relevant diseases, the development of specific therapeutic antibodies targeted to TF is extremely beneficial for the diagnosis, treatment and prevention of pathological features resulted from vascular proliferation, abnormal coagulation, and the like, which are caused by TF in various diseases such as cancer, thrombosis and inflammation.

Contents of Invention

The objective of the present invention is to provide a TF antibody, which specifically targets human TF, has an activity of inhibiting tumor growth and metastasis, and has an anticoagulant activity, an activity of inhibiting the production of activated coagulation factor X (FXa), and the like.

In the first aspect, the present invention provides the heavy chain variable region of an antibody, comprising the following three complementary determining regions (CDRs):

CDR1 as set forth in SEQ ID NO:1,
CDR2 as set forth in SEQ ID NO:2, and
CDR3 as set forth in SEQ ID NO:3;

wherein, any amino acid sequence of said amino acid sequences further includes a derivative sequence that is resulted from the optional addition, deletion, modification and/or substitution of at least amino acid, and that can retain a TF-binding activity.

In the second aspect, the present invention provides the heavy chain of an antibody, wherein the heavy chain has the heavy chain variable region according to the first aspect.

In another preferred example, the heavy chain variable region has the amino acid sequence as set forth in SEQ ID NO:7.

In the third aspect, the present invention provides the light chain variable region of an antibody, wherein the light chain variable region has complementary determining regions (CDRs) selected from the group consisting of:

CDR1' as set forth in SEQ ID NO:4,
CDR2' as set forth in SEQ ID NO:5, and
CDR3' as set forth in SEQ ID NO:6;

a derivative sequence of any amino acid sequence of said amino acid sequences that is resulted from the addition, deletion, modification and/or substitution of at least one amino acid, and that has a TF-binding activity.

In the fourth aspect, the present invention provides the light chain of an antibody, wherein the light chain has the light chain variable region according to the third aspect.

In another preferred example, the light chain variable region has the amino acid sequence as set forth in SEQ ID NO:8.

In the fifth aspect, the present invention provides an antibody having:

(1) the heavy chain variable region according to the first aspect; and/or
(2) the light chain variable region according to the third aspect;

or, the antibody has: the heavy chain according to the second aspect; and/or the light chain according to the fourth aspect.

In another preferred example, the antibody is selected from: an animal-derived antibody, a chimeric antibody, a humanized antibody, or a combination thereof.

In another preferred example, the number of the added, deleted, modified and/or substituted amino acids does not exceed 40% of the total number of the amino acids of the initial amino acid sequence.

In another preferred example, the number of the added, deleted, modified and/or substituted amino acids is 1-7.

In another preferred example, the sequence resulted from the addition, deletion, modification and/or substitution of at least one amino acid is an amino acid sequence having a homology of at least 80%.

In another preferred example, the sequence resulted from the addition, deletion, modification and/or substitution of at least one amino acid has one or more of an activity of inhibiting TF-related signal pathway, an anticoagulant activity, and an activity of inhibiting the production of FXa.

In another preferred example, the antibody is selected from the group consisting of: TF-mAb-SC1, TF-mAb-Ch, TF-mAb-H39, and TF-mAb-H44.

In the sixth aspect, the present invention provides use of the antibody according to the present invention, for (a) manufacture of a diagnostic agent; and/or (b) manufacture of a medicament for preventing and/or treating a TF-related disease.

In another preferred example, the TF-related disease is selected from: tumorigenesis, tumor growth and/or metastasis, a thrombosis-related diseases, inflammation, a metabolism-related disease, or a combination thereof.

In another preferred example, the tumor is a tumor with high TF expression.

In another preferred example, the expression "high TF expression" means that when the TF transcript and/or protein level L1 in a tumor tissue is compared with the transcript and/or protein level L0 in a normal tissue, $L1/L0 \geq 2$, preferably $\geq 3$.

In another preferred example, the tumor is selected from the group consisting of: triple-negative breast cancer, pancreatic cancer, lung cancer and malignant glioma.

In another preferred example, the drug is an antibody-drug conjugate.

In the seventh aspect, the present invention provides a recombinant protein having:

(i) the heavy chain variable region according to the first aspect, the heavy chain according to the second aspect, the light chain variable region according to the third aspect, the light chain according to the fourth aspect, or the antibody according to the fifth aspect; and (ii) optionally a tag sequence that assists in expression and/or purification.

In the eighth aspect, the present invention provides a polynucleotide encoding a polypeptide selected from:

(1) the heavy chain variable region according to the first aspect, the heavy chain according to the second aspect, the light chain variable region according to the third aspect, the light chain according to the fourth aspect, or the antibody according to the fifth aspect; or (2) the recombinant protein according to the seventh aspect.

In the ninth aspect, the present invention provides a vector comprising the polynucleotide according to the eighth aspect.

In the tenth aspect, the present invention provides a genetically engineered host cell comprising the vector according to the ninth aspect or having the polynucleotide according to the eighth aspect integrated in genome.

In the eleventh aspect, the present invention provides an antibody-drug conjugate comprising:

(a) an antibody moiety that is selected from: the heavy chain variable region according to the first aspect, the heavy chain according to the second aspect, the light chain variable region according to the third aspect, the light chain according to the fourth aspect, the antibody according to the fifth aspect, or a combination thereof; and (b) a conjugation moiety conjugated to the antibody moiety, wherein the conjugation moiety is selected from: a detectable marker, a drug, a toxin, a cytokine, a radionuclide, an enzyme, or a combination thereof.

In another preferred example, the antibody moiety is conjugated to the conjugation moiety via a chemical bond or a linker.

In another preferred example, the antibody moiety in the antibody-drug conjugate is selected from the group consisting of: TF-mAb-SC1, TF-mAb-Ch, or TF-mAb-H29 to TF-mAb-H48; more preferably, the antibody moiety is selected from the group consisting of: TF-mAb-H39, and TF-mAb-H44.

In the twelfth aspect, the present invention provides an immune cell that expresses the antibody according to the fifth aspect of the present invention or has the antibody according to the fifth aspect of the present invention exposed outside the cell membrane.

In another preferred example, the immune cell includes NK cell, T cell.

In another preferred example, the immune cell is a human immune cell.

In another preferred example, the antibody is a single chain antibody.

In the thirteenth aspect, the present invention provides a pharmaceutical composition, comprising:
(i) an active ingredient, the active ingredient is selected from: the heavy chain variable region according to the first aspect, the heavy chain according to the second aspect, the light chain variable region according to the third aspect, the light chain according to the fourth aspect, the antibody according to the fifth aspect, the recombinant protein according to the seventh aspect, the antibody-drug conjugate according to the eleventh aspect, the immune cell according to the twelfth aspect, or a combination thereof; and
(ii) a pharmaceutically acceptable carrier.

In the fourteenth aspect, the present invention provides use of an active ingredient for manufacture of a medicament, an agent, a test panel, or a kit, wherein the active ingredient is selected from: the heavy chain variable region according to the first aspect, the heavy chain according to the second aspect, the light chain variable region according to the third aspect, the light chain according to the fourth aspect, or the antibody according to the fifth aspect, the recombinant protein according to the seventh aspect, the antibody-drug conjugate according to the eleventh aspect, the immune cell according to the twelfth aspect, or a combination thereof.

In another preferred example, the agent, the test panel or the kit is used for:
(1) detecting TF protein in a sample; and/or
(2) detecting endogenous TF protein in a tumor cell; and/or
(3) detecting a tumor cell expressing TF protein;
and the medicament is used for treating or preventing a disease such as a TF protein-expressing tumor, a thrombotic disease, obesity and diabetes.

In the fifteenth aspect, the present invention provides a method for determining (including diagnostically or non-diagnostically determining) TF protein in a sample in vitro, comprising the steps of:
(1) contacting the sample with the antibody according to the present invention in vitro; and
(2) determining whether an antigen-antibody complex is formed, wherein the formation of a complex indicates the presence of TF protein in the sample.

In the sixteenth aspect, the present invention provides a test panel comprising: a substrate (a support plate) and a test strip, wherein the test strip comprises the antibody according to the fifth aspect or the immunoconjugate according to the eleventh aspect.

In the seventeenth aspect, the present invention provides a kit, characterized in that the kit comprises:
(1) a first container comprising the antibody according to the present invention; and/or
(2) a second container comprising a secondary antibody against the antibody according to the present invention;
or,
the kit comprises the test panel according to the sixteenth aspect.

In then eighteenth aspect, the present invention provides a method for preparing a recombinant polypeptide, comprising:
(a) culturing the host cell according to the tenth aspect under conditions suitable for expression;
(b) separating the recombinant polypeptide from the culture, wherein the recombinant polypeptide is the antibody according to the fifth aspect or the recombinant protein according to the seventh aspect.

In the nineteenth aspect, the present invention provides a method for treating a tumor, a thrombotic disease, an inflammatory disease and/or a metabolic disease, comprising: using (e.g. administering to a subject in need thereof) the antibody according to the fifth aspect, an antibody-drug conjugate of the antibody, or a CAR-T cell expressing the antibody, or a combination thereof.

In another preferred example, the metabolic disease includes: obesity, or diabetes.

In the twentieth aspect, the present invention provides an anti-TF antibody, wherein the antibody has an $EC_{50}$ of 0.005-0.10 nM, preferably 0.005-0.05 nM, more preferably 0.01-0.03 nM or 0.01-0.02 nM, for the affinity to human TF protein.

In another preferred example, the antibody does not bind to wild-type mouse TF protein.

In another preferred example, the antibody has one or more characteristics selected from the group consisting of:
(a) inhibiting migration or metastasis of tumor cells; and
(b) inhibiting tumor growth.

In another preferred example, the antibody is TF-mAb-SC1, TF-mAb-Ch, or TF-mAb-H29 to TF-mAb-H48; preferably, the antibody is selected from the group consisting of: TF-mAb-SC1, TF-mAb-Ch, TF-mAb-H39, and TF-mAb-H44.

In the twenty-first aspect, the present invention provides a method for preparing a humanized or chimeric antibody, comprising the steps of:
after cloning the nucleotide sequence of a murine antibody variable region according to the present invention into an expression vector containing a human antibody constant region, expressing the human-mouse chimeric antibody by transfecting animal cells;
after cloning the nucleotide sequence of an antibody variable region comprising human FR region according to the present invention into an expression vector comprising a human antibody constant region, expressing the humanized antibody by transfecting animal cells.

In another preferred example, the antibody is a partially or completely humanized monoclonal antibody.

In the twenty-second aspect, the present invention provides a method for inhibiting metastasis of tumor cells, characterized by comprising the step of: administering the antibody according to the present invention, an antibody-drug conjugate of the antibody, or a CAR-T cell expressing the antibody, to a subject in need thereof.

It should be understood that within the scope of the present invention, the above-mentioned technical features of the present invention and the technical features specifically described below (e.g. in Examples) may be combined with each other so as to constitute a new or preferred technical solution. For the purpose of space saving, these combinations are not described here any more.

DESCRIPTION OF THE DRAWINGS

FIG. 4 shows the restriction enzyme digestion result of the expression plasmid of the human-mouse chimeric antibody (TF-mAb-Ch) by single enzyme digestion and double enzyme digestion, wherein

FIG. 5 shows the binding affinity of TF-mAb-SC1 to cancer cell surface TF, wherein

FIG. 17 shows the determination of the activity of TF-mAb-SC1 for inhibiting the hematogenous migration ability of MDA-MB-231-luc cells in mice, and the statistic result of the fluorescence intensity thereof.

FIG. 18A shows the representative images and statistical analysis on the formation of MDA-MB-231 tumor metastatic foci on the lungs of mice and FIG. 18B shows the result of statistical analysis on the weight of lungs in each group.

FIG. 19 shows the result on the internalization of TF-mAb-SC1 to lysosome by MDA-MB-231 cells as observed under a laser confocal microscope.

SPECIFIC MODES FOR CARRYING OUT THE INVENTION

Figure 1:
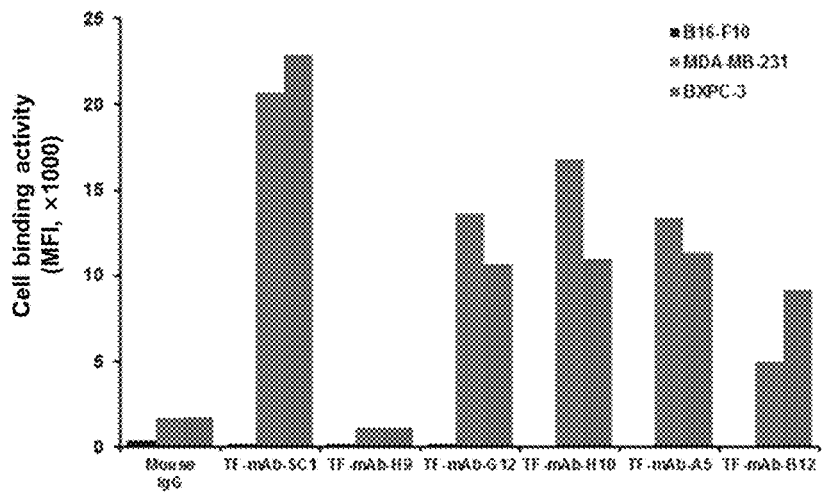
FIG. 1 shows the binding activity of a series of original anti-human TF monoclonal antibodies (original hybridomas) to human TF-positive (MDA-MB-231 and BxPC-3), and murine TF-positive (B16-F10) cells, wherein TF-mAb-SC1 showed the best binding activity at a concentration of 10 μg/mL.

The inventors obtained an anti-TF monoclonal antibody (TF-mAb-SC1) unexpectedly by conducting extensive and deep research and a large number of screenings, and the experimental results show that the monoclonal antibody against TF protein is an IgG2b antibody. The antibody can bind to TF antigen with high specificity and high affinity (the $EC_{50}$ is approximately 0.019 nM as determined by ELISA), and the antibody has a significant antitumor activity, and has no obvious toxic side-effects on mammals themselves. Further, the chimeric antibody, the humanized antibody, and the corresponding ADC, which are obtained based on the TF-mAb-SC1, also have excellent characteristics. The present invention has been accomplished on the basis of these.

Antibody

As used herein, the term "antibody" or "immunoglobulin" are heterotetrameric glycoproteins of about 150,000 Da having the same structural characteristics, which consist of two identical light chains (L) and two identical heavy chains (H). Each light chain is linked to a heavy chain via a covalent disulfide bond, and different immunoglobulin isotypes have different numbers of disulfide bonds between the heavy chains. There are also regularly spaced intrachain disulfide bonds in each heavy and each light chain. Each heavy chain has a variable region (VH) at one end, followed by a plurality of constant regions. Each light chain has a variable region (VL) at one end and a constant region at the other end; the constant region of a light chain corresponding to the first constant region of a heavy chain, and the variable region of a light chain corresponding to the variable region of a heavy chain. Special amino acid residues form an interface between the variable regions of a light chain and a heavy chain.

As used herein, the term "variable" means that antibodies are different from each other in terms of sequence in certain parts of variable regions, which is responsible for the binding and specificity of various specific antibodies to their specific antigens. However, the variability is not distributed evenly throughout the variable regions of an antibody. It is concentrated in three segments called complementarity determining regions (CDRs) or hypervariable regions in the light and heavy chain variable regions. The conserved parts of variable regions are called framework regions (FRs). Each of the variable regions of naturally occurring heavy and light chains comprises four FR regions, which are generally in β-sheet configuration, joined by the three CDRs forming a linking loop, and in some cases, may form a partial β-sheet structure. The CDRs in each chain are closely linked together via the FR regions, and together with the CDRs of the other chain, form the antigen binding site of an antibody (see Kabat et al., NIH Publ. No. 91-3242, Vol. I, pp. 647-669 (1991)). The constant regions are not directly involved in the binding of an antibody to an antigen, however, they exhibit different effects and functions, for example, are involved in the antibody-dependent cytotoxicity of an antibody.

The "light chain" of a vertebrate antibody (immunoglobulin) can be classified into one of the two obviously different classes (referred to as κ and λ) depending on the amino acid sequence of its constant region. Immunoglobulins can be classified into different classes depending on the amino acid sequences of their heavy chain constant regions. There are mainly five classes of immunoglobulins: IgA, IgD, IgE, IgG, and IgM, some of which can be further classified into subclasses (isotypes), such as IgG1, IgG2, IgG3, IgG4, IgA, and IgA2. The heavy chain constant regions corresponding to different classes of immunoglobulins are called α, δ, ε, γ, and μ, respectively. The subunit structures and three-dimensional configurations of different classes of immunoglobulins are well known for those skilled in the art.

In general, the antigen binding characteristics of an antibody can be described by three specific regions located in the heavy and light chain variable regions, called complementarity determining regions (CDRs), which divide the variable region into four framework regions (FRs); the amino acid sequences of the four FRs are relatively conservative and are not directly involved in the binding reaction. These CDRs form a ring structure, and approach to each other in the steric structure via the β-sheets formed by the FRs between them, and the CDRs on the heavy chain and the CDRs on the corresponding light chain constitute the antigen-binding site of an antibody. By comparison of the amino acid sequences of antibodies of the same type, it can be determined which amino acids form FRs or CDRs.

The present invention includes not only an intact antibody, but also the fragments of the antibody having immunological activity or a fusion protein formed by the antibody and another sequence. Therefore, the present invention also includes fragments, derivatives and analogs of the antibody.

In the present invention, antibodies include murine, chimeric, humanized or fully human antibodies as prepared by techniques well known to those skilled in the art. Recombinant antibodies, such as chimeric and humanized monoclonal antibodies, including human and non-human portions, can be obtained by standard DNA recombination techniques, all of which are useful antibodies. A chimeric antibody is a molecule in which different portions are derived from different animal species, for example, a chimeric antibody having a variable region from a monoclonal antibody from a mouse, and a constant region from a human immunoglobulin (see, for example, U.S. Pat. Nos. 4,816,567 and 4,816,397, which are incorporated herein by reference in its entirety). A humanized antibody refers to an antibody molecule derived from a non-human species, which has one or more complementarity determining regions (CDRs) derived from a non-human species and framework regions derived from a human immunoglobulin molecule (see U.S. Pat. No. 5,585,089, which is incorporated herein by reference in its entirety). These chimeric and humanized monoclonal antibodies can be prepared by recombinant DNA techniques well known in the art.

In the present invention, an antibody may be monospecific, bispecific, trispecific, or multispecific.

In the present invention, the antibody according to the present invention further include a conservative variant thereof, which refers to a polypeptide formed by substitution of at most 10, preferably at most 8, more preferably at most 5, and most preferably at most 3 amino acids with similar amino acids, as compared to the amino acid sequence of the antibody according to the present invention. These conservative variant polypeptide is preferably prepared by the amino acid substitution according to Table A.

TABLE A

| Initial residue | Representative substitution | Preferred substitution |
|---|---|---|
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |

TABLE A-continued

| Initial residue | Representative substitution | Preferred substitution |
|---|---|---|
| Lys (K) | Arg; Gln; Asn | Arg |
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala | Leu |

Anti-TF Antibodies

The present invention provides an antibody having a high specificity and a high affinity for TF, comprising a heavy chain and a light chain, wherein the heavy chain comprises the amino acid sequence of a heavy chain variable region (VH), and the light chain comprises the amino acid sequence of a light chain variable region (VL).

Preferably, the CDRs for the amino acid sequence of the heavy chain variable region (VH) and the amino acid sequence of the light chain variable region (VL) are selected from:

a1) SEQ ID No: 1;
a2) SEQ ID No: 2;
a3) SEQ ID No: 3;
a4) SEQ ID No: 4;
a5) SEQ ID No: 5;
a6) SEQ ID No: 6;
a7) a sequence that is resulted from the addition, deletion, modification and/or substitution of at least one amino acid of any amino acid sequence of said amino acid sequences, and has TF-binding affinity.

In another preferred example, the sequence resulted from the addition, deletion, modification and/or substitution of at least amino acid is preferably an amino acid sequence having a homology of at least 80%, preferably at least 85%, more preferably at least 90%, most preferably at least 95%.

Preferably, the antibody has the activity of inhibiting the TF-related signal pathway; has an anticoagulant activity; has an activity of inhibiting FXa production, or a combination thereof.

The antibody according to the present invention may be a double-chain or single-chain antibody, and may be selected from the group consisting of an animal-derived antibody, a chimeric antibody, and a humanized antibody; more preferably, may be selected from the group consisting of a humanized antibody, and a human-animal chimeric antibody; and more preferably, may be a fully human antibody.

The antibody derivative according to the present invention may be a single-chain antibody, and/or an antibody fragment, for example, Fab, Fab', (Fab')2 or other antibody derivatives known in the art, etc., and may be any one or more of IgA, IgD, IgE, IgG and IgM antibodies or other subtype antibodies.

In the present invention, the animal is preferably a mammal, such as mouse.

The antibody according to the present invention may be a chimeric antibody targeted to human TF, a humanized antibody, a CDR grafted and/or modified antibody.

In a preferred example of the present invention, any one or more sequences of SEQ ID No: 1-SEQ ID No: 3, or sequences thereof that are resulted from the addition, deletion, modification and/or substitution of at least one amino acid and have a TF-binding affinity, are located in the CDRs of heavy chain variable region (VH).

In a preferred example of the present invention, any one or more sequences of SEQ ID No: 4-SEQ ID No: 6, or sequences thereof that are resulted from the addition, deletion, modification and/or substitution of at least one amino acid and have a TF-binding affinity, are located in the CDRs of light chain variable region (VL).

In a more preferred example of the present invention, VH CDR1, CDR2, CDR3 are independently selected from any one or more sequences of SEQ ID No: 1-SEQ ID No: 3, or sequences thereof that are resulted from the addition, deletion, modification and/or substitution of at least one amino acid and have a TF-binding affinity; VL CDR1, CDR2, CDR3 are independently selected from any one or more sequences of SEQ ID No: 4-SEQ ID No: 6, or sequences thereof that are resulted from the addition, deletion, modification and/or substitution of at least one amino acid and have a TF-binding affinity.

In the present invention, the number of the added, deleted, modified and/or substituted amino acids, preferably does not exceed 40%, more preferably does not exceed 35%, is more preferably 1-33%, is more preferably 5-30%, is more preferably 10-25%, and is more preferably 15-20% of the total number of the amino acids of the initial amino acid sequence.

In the present invention, more preferably, the number of the added, deleted, modified and/or substituted amino acids, may be 1-7, more preferably 1-5, more preferably 1-3, more preferably 1-2.

In another preferred example, the antibody targeted to TF is TF-mAb-SC1 (the original name of which is TF-mAb).

In another preferred example, the amino acid sequence of the heavy chain variable region (VH) of the antibody TF-mAb-SC1 is the amino acid sequence as set forth in SEQ ID NO: 7.

In another preferred example, the amino acid sequence of the light chain variable region (V-Kappa) of the antibody TF-mAb-SC1 is the amino acid sequence as set forth in SEQ ID NO: 8.

Preparation of Antibodies

The sequence of the DNA molecule for the antibody or a fragment thereof according to the present invention can be obtained by conventional techniques, for example, methods such as PCR amplification or genomic library screening. In addition, the sequences encoding light chain and heavy chain can be fused together, to form a single-chain antibody.

Once a relevant sequence is obtained, recombination methods can be used to obtain the relevant sequence in large quantities. This is usually carried out by cloning the sequence into a vector, transforming a cell with the vector, and then separating the relevant sequence from the proliferated host cell by conventional methods.

In addition, a relevant sequence can be synthesized artificially, especially when the fragment is short in length. Usually, several small fragments are synthesized first, and then are linked together to obtain a fragment with a long sequence.

It has been possible now to obtain a DNA sequence encoding the antibody (or a fragment thereof, or a derivative thereof) according to the present invention completely by chemical synthesis. Then, the DNA sequence can be introduced into various existing DNA molecules (or, for example, vectors) and cells known in the art. In addition, mutations can also be introduced into the protein sequence according to the present invention by chemical synthesis.

The present invention further relates to a vector comprising said suitable DNA sequence and a suitable promoter or a control sequence. These vectors can be used to transform suitable host cells to enable them to express protein.

The host cell can be a prokaryotic cell, such as a bacterial cell; or a lower eukaryotic cell, such as a yeast cell; or a higher eukaryotic cell, such as a mammalian cell. Preferred animal cells include, but are not limited to, CHO-S, HEK-293 cells.

In general, under conditions suitable for expression of the antibody according to the present invention, the host cell obtained is cultured. Then, the antibody according to the present invention is purified by using conventional immunoglobulin purification steps, for example, the conventional separation and purification means well known to those skilled in the art, such as protein A-Sepharose, hydroxyapatite chromatography, gel electrophoresis, dialysis, ion exchange chromatography, hydrophobic chromatography, molecular sieve chromatography or affinity chromatography.

The monoclonal antibody obtained can be identified by conventional means. For example, the binding specificity of a monoclonal antibody can be determined by immunoprecipitation or an in vitro binding assay (such as radioimmunoassay (RIA) or enzyme-linked immunosorbent assay (ELISA)). The binding affinity of a monoclonal antibody can be determined by, for example, the Scatchard analysis (Munson et al., Anal. Biochem., 107: 220 (1980)).

The antibody according to the present invention can be expressed in a cell or on the cell membrane, or is secreted extracellularly. If necessary, the recombinant protein can be separated and purified by various separation methods according to its physical, chemical, and other properties. These methods are well known to those skilled in the art. Examples of these methods include, but are not limited to, conventional renaturation treatment, treatment with a protein precipitant (salting out method), centrifugation, osmotic bacteria disruption, ultrasonic treatment, ultracentrifugation, molecular sieve chromatography (gel filtration), adsorption chromatography, ion exchange chromatography, high performance liquid chromatography (HPLC), various other liquid chromatographic techniques, and combinations of these methods.

Antibody-Drug Conjugate (ADC)

The present invention also provides an antibody-drug conjugate (ADC) based on the antibody according to the present invention.

Typically, the antibody-drug conjugate comprises the antibody and an effector molecule, wherein the antibody is conjugated to the effector molecule, and chemical conjugation is preferred. Preferably, the effector molecule is a therapeutically active drug. In addition, the effector molecule may be one or more of a toxic protein, a chemotherapeutic drug, a small-molecule drug or a radionuclide.

The antibody according to present invention and the effector molecule may be coupled by a coupling agent. Examples of the coupling agent may be any one or more of a non-selective coupling agent, a coupling agent utilizing a carboxyl group, a peptide chain, and a coupling agent utilizing a disulfide bond. The non-selective coupling agent refers to a compound that results in a linkage between an effector molecule and an antibody via a covalent bond, such as glutaraldehyde, etc. The coupling agent utilizing a carboxyl group may be any one or more of cis-aconitic anhydride coupling agents (such as cis-aconitic anhydride) and acyl hydrazone coupling agents (the coupling site is acyl hydrazone).

Certain residues on an antibody (such as Cys or Lys, etc.) are used to link a variety of functional groups, including imaging agents (such as chromophores and fluorophores), diagnostic agents (such as MRI contrast agents and radioisotopes), stabilizers (such as poly(ethylene glycol)) and therapeutic agents. An antibody can be conjugated to a functional agent to form a conjugate of the antibody-functional agent. A functional agent (e.g. a drug, a detection reagent, a stabilizer) is conjugated (covalently linked) to an antibody. A functional agent can be linked to an antibody either directly or indirectly via a linker.

Antibodies can be conjugated to drugs to form antibody-drug conjugates (ADCs). Typically, an ADC comprises a linker between a drug and an antibody. The linker can be a degradable or non-degradable linker. Typically, degradable linkers are easily degraded in an intracellular environment, for example, the linker is degraded at the target site, thereby releasing the drug from the antibody. Suitable degradable linkers include, for example, enzyme-degradable linkers, including peptidyl-containing linkers that can be degraded by protease (e.g. lysosomal protease or endosomal protease) in a cell, or sugar linkers, for example, glucuronide-containing linkers that can be degraded by glucuronidase. Peptidyl linkers may include, for example, dipeptides, such as valine-citrulline, phenylalanine-lysine or valine-alanine. Other suitable degradable linkers include, for example, pH sensitive linkers (e.g. linkers that are hydrolyzed at a pH of below 5.5, such as hydrazone linkers) and linkers that are degraded under reducing conditions (e.g. disulfide-bond linkers). A non-degradable linker typically releases a drug under conditions that the antibody is hydrolyzed by protease.

Prior to linkage to an antibody, a linker has a reactive group capable of reacting with certain amino acid residues, and the linkage is achieved by the reactive group. A thiol-specific reactive group is preferred, which includes, for example, a maleimide compound, a halogenated (e.g. iodo-, bromo- or chloro-substituted) amide; a halogenated (e.g. iodo-, bromo- or chloro-substituted) ester; a halogenated (e.g. iodo-, bromo- or chloro-substituted) methyl ketone, a benzyl halide (e.g. iodide, bromide or chloride); vinyl sulfone, pyridyl disulfide; a mercury derivative such as 3,6-di-(mercurymethyl)dioxane, wherein the counter ion is $CH_3COO^-$, $Cl^-$ or $NO_3^-$; and polymethylene dimethyl sulfide thiosulfonate. The linker may include, for example, a maleimide linked to an antibody via thiosuccimide.

A drug may be any cytotoxic, cytostatic or immunosuppressive drug. In an embodiment, an antibody is linked to a drug via a linker, and the drug has a functional group that can form a bond with the linker. For example, a drug may have an amino group, a carboxyl group, a thiol group, a hydroxyl group, or a ketone group that can form a bond with a linker. When a drug is directly linked to a linker, the drug has a reactive group before being linked to an antibody.

Useful drugs include, for example, anti-tubulin drugs, DNA minor groove binding agents, DNA replication inhibitors, alkylating agents, antibiotics, folic acid antagonists, antimetabolites, chemotherapy sensitizers, topoisomerase inhibitors, vinca alkaloids, etc. Examples of particularly useful cytotoxic drugs include, for example, DNA minor groove binding agents, DNA alkylating agents, and tubulin inhibitors; typical cytotoxic drugs include, for example, auristatins, camptothecins, docamycin/duocarmycins, etoposides, maytansines and maytansinoids (e.g. DM1 and DM4), taxanes, benzodiazepines or benzodiazepine containing drugs (e.g. pyrrolo[1,4]benzodiazepines (PBDs), indolinobenzodiazepines and oxazolidinobenzodiazepines), and vinca alkaloids.

In the present invention, a drug-linker can be used to form an ADC in a simple step process. In other embodiments, a bifunctional linker compound can be used to form an ADC in a two-step or multi-step process. For example, a cysteine residue is reacted with the reactive moiety of a linker in a first step, and then the functional group on the linker is reacted with a drug in the subsequent step, so as to form an ADC.

In general, the functional group on a linker is selected so that it can specifically react with the suitable reactive group on a drug moiety. As a non-limiting example, an azide-based moiety can be used to specifically react with the reactive alkynyl group on a drug moiety. The drug is covalently bound to the linker by 1,3-dipolar cycloaddition between the azide and alkynyl group. Other useful functional groups include, for example, ketones and aldehydes (suitable for reacting with hydrazides and alkoxyamines), phosphines (suitable for reacting with azides); isocyanates and isothiocyanates (suitable for reacting with amines and alcohols); and activated esters, for example, N-hydroxysuccinimide esters (suitable for reacting with amines and alcohols). These and other linkage strategies, for example, those described in Bioconjugation Technology ($2^{nd}$ Edition (Elsevier)), are well known to those skilled in the art. Those skilled in the art could understand that when a complementary pair of reactive functional groups are selected for a selective reaction between a drug moiety and a linker, each member of the complementary pair can be used for the linker, and can also be used for the drug.

The present invention further provides a method for preparing an ADC, which may further comprise: under conditions sufficient to form an antibody-drug conjugate (ADC), binding an antibody to a drug-linker compound.

In certain embodiments, the method according to the present invention comprises: under conditions sufficient to form an antibody-linker conjugate, binding an antibody to a bifunctional linker compound. In these embodiments, the method according to the present invention further comprises: under conditions sufficient to covalently link the drug moiety to the antibody via a linker, binding the antibody-linker conjugate to the drug moiety.

In some embodiments, an antibody-drug conjugate (ADC) has a formula as follows:

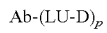

wherein:
Ab is an antibody,
LU is a linker;
D is a drug;
and the subscript p is an value selected from 1 to 8.

Detection Application and Kit

The antibody or an ADC thereof according to the present invention can be used in detection application, for example, for use in detection of a sample so as to provide diagnostic information.

In the present invention, the specimen (sample) used includes a cell, a tissue sample and a biopsy specimen. The term "biopsy" used in the present invention should include all kinds of biopsies known by those skilled in the art. Therefore, the biopsy specimen used in the present invention may include, for example, a resected sample of a tumor, and a tissue sample prepared by endoscopic methods or puncture or needle puncture biopsy of an organ.

The sample used in the present invention includes a fixed or preserved cell or tissue sample.

The present invention further provides a kit only comprising the antibody (or a fragment thereof) according to the present invention; in a preferred example of the present invention, the kit further comprises containers, instructions, buffers, etc. In the preferred examples, the antibody according to the present invention can be immobilized on a test panel.

Application

The present invention further provides use of the antibody according to the present invention, for example, for manufacture of a diagnostic agent, or for manufacture of a medicament for preventing and/or treating a TF-related disease. The TF-related disease includes tumorigenesis, tumor growth and/or metastasis, a thrombosis-related disease, inflammation, a metabolism-related disease, etc.

Use of the antibody, ADC or CAR-T according to the present invention includes (but is not limited to):

(i) for diagnosis, prevention and/or treatment of tumorigenesis, tumor growth and/or metastasis, particularly, a tumor with high TF expression, wherein the tumor includes (but is not limited to): breast cancer (e.g. triple-negative breast cancer), pancreatic cancer, lung cancer, malignant glioma, gastric cancer, liver cancer, esophageal cancer, kidney cancer, colorectal cancer, bladder cancer, prostate cancer, endometrial cancer, ovarian cancer, cervical cancer, leukemia, bone marrow cancer, angiosarcoma, etc.; particularly, triple-negative breast cancer, pancreatic cancer, malignant glioma and lung cancer; more preferably triple-negative breast cancer and/or pancreatic cancer;

(ii) for diagnosis, prevention and/or treatment of a thrombosis-related disease, wherein the thrombosis-related diseases includes (but is not limited to): atherosclerosis, acute coronary syndrome, acute myocardial infarction, stroke, hypertension, deep vein thrombosis, pulmonary embolism, renal embolism and arterial surgery, thrombosis caused by coronary artery bypass grafting, etc.;

(iii) for diagnosis, prevention and/or treatment of inflammation, wherein the inflammation includes (but is not limited to): rheumatic arthritis, osteoarthritis, ankylosing spondylitis, gout, Lytle syndrome, psoriasis arthritis, infectious arthritis, tuberculous arthritis, viral arthritis, fungal arthritis, glomerular Nephritis, systemic lupus erythematosus, Crohn's disease, ulcerative colitis, acute lung injury, chronic obstructive pulmonary disease, and idiopathic pulmonary fibrosis;

(iv) for diagnosis, prevention and/or treatment of a metabolism-related disease, wherein the metabolism-related disease includes (but is not limited to): diabetes, diet-induced obesity, adipose inflammation, etc.

Pharmaceutical Composition

The present invention further provides a composition. In the preferred examples, the composition is a pharmaceutical composition comprising the antibody, or an active fragment, a fusion protein or an ADC thereof, or a corresponding CAR-T cell, and a pharmaceutically acceptable carrier. In general, these substances may be formulated in a non-toxic, inert and pharmaceutically acceptable aqueous carrier medium, wherein the pH is generally about 5-8, preferably, pH is about 6-8, though the pH value may be varied depending on the nature of the substances to be formulated and the condition to be treated. The formulated pharmaceutical composition may be administered by conventional routes, including (but not limited to): intratumoral, intraperitoneal, intravenous, or topical administration.

The antibody according to the present invention may also be expressed from a nucleotide sequence in a cell and be used in a cell therapy, for example, the antibody is used in Chimeric Antigen Receptor T cell immunotherapy (CAR-T), etc.

The pharmaceutical composition according to the present invention may be directly used to bind a TF protein molecule, and therefore may be used to prevent and treat a disease such as tumor. In addition, concomitant therapeutic agents may also be used simultaneously.

The pharmaceutical composition according to the present invention comprising a safe and effective amount (e.g. 0.001-99 wt %, preferably 0.01-90 wt %, preferably 0.1-80 wt %) of the monoclonal antibody according to the present invention (or a conjugate thereof) and a pharmaceutically acceptable carrier or excipient. Such carriers include (but are not limited to): saline, buffers, glucose, water, glycerol, ethanol, and a combination thereof. Pharmaceutical preparations should correspond to the administration modes. The pharmaceutical composition according to the present invention can be prepared in the form of an injection, for example, by a conventional method using physiological saline or an aqueous solution containing glucose and other adjuvants. A pharmaceutical composition, for example, an injection and a solution, should be prepared under aseptic conditions. The administration amount of an active ingredient is a therapeutically effective amount, for example, about 1 µg per kilogram of body weight to about 5 mg per kilogram of body weight daily. In addition, the polypeptide according to the present invention may also be used in combination with an additional therapeutic agent.

When a pharmaceutical composition is used, a safe and effective amount of an immunoconjugate is administered to a mammal, wherein the safe and effective amount is generally at least about 10 µg per kilogram of body weight, and in most cases, no more than about 50 mg per kilogram of body weight, Preferably, the dose is from about 10 µg per kilogram of body weight to about 20 mg per kilogram of body weight. Of course, a specific dose should also depend on the factors such as administration route and physical conditions of a patient, which are within the skills of skilled physicians.

The main advantages of the present invention include:

(a) the antibody according to the present invention has an excellent bioactivity and specificity, and has a very high affinity (the $EC_{50}$ is 0.01-0.03 nM as determined by ELISA); in addition, it has a good binding affinity for cell surface TF, and may be used as an TF-targeting antibody;

(b) the humanized antibody according to the present invention not only has an activity comparable to that of immune antibodies, but also has a lower immunogenicity;

(c) both the antibody and the ADC according to the present invention have a significant anti-tumor activity, and have no obvious toxic side-effects on mammals themselves; and (d) the antibody and the ADC according to the present invention not only have significant therapeutic effects in tumor models, but also are applicable to other high TF expression-associated diseases, such as thrombotic diseases, and metabolic diseases.

The present invention is further described by reference to the following particular examples. It should be understood that the following examples are only used to describe the present invention, rather than limiting the scope of the present invention. The experimental methods in the following examples, the specific conditions of which are not indicated, are usually carried out according to conventional conditions, for example, the conditions described in Sambrook et al., Molecular Cloning: Laboratory Manual (New York: Cold Spring Harbor Laboratory Press, 1989), or the conditions recommended by the manufacturers. Unless otherwise specified, percentages and parts refer to percentages by weight and parts by weight. Cell lines are the conventional products that are commercially available or are purchased from ATCC, and all the plasmids are the products that are commercially available.

Example 1 Discovery and Preparation of a Monoclonal Antibody Targeted to Human TF Step ①, Preparation of Hybridoma Cells:

Firstly, 8-week old Balb/c female mice were immunized with the extracellular domain of human TF protein (UniProtKB/Swiss-Prot: P13726.1, the amino acids from positions 34 to 251), wherein the extracellular domain protein of TF was used in an amount of 100 µg/mouse, to prepare the immunized splenocytes; murine myeloma cells (SP2/0) and feeder cells were prepared timely for the purpose of fusion.

After said three cells were prepared, the fusion of splenocytes and SP2/0 cells was mediated by PEG, PEG was removed, and the resultant cells were re-suspended in HAT complete medium containing feeder cells, and were seeded and cultured in a 96-well plate. Positive wells were screened by ELISA. Finally, the cells in the positive wells were subjected to clonal culture by limiting dilution method, and the cells, which had a high titer and good morphology and grew in a monoclonal manner, were screened by ELISA or immunofluorescence technique. The cells grew in a monoclonal manner were further subjected to subcloning screening until the positive cloning rate was 100% for three times of consecutive screenings. That is, the cell line could be subjected to amplification culture and library construction.

Step ②, Preparation of the Ascites of a Murine Monoclonal Antibody Targeted to Human TF:

The hybridoma cells screened out in Step ① were subjected to amplification culture. After adaptive raising, pristane (0.5 mL/mouse) was injected into the abdominal cavity of mice to provide a favorable environment for the growth of hybridoma cells. 7-10 days later, $10 \times 10^6$ hybridoma cells were injected into the abdominal cavity of each mouse. The mice were observed everyday for the production of ascites and the mental states since the seventh day, and the ascites was collected, centrifuged to remove fats, and cryopreserved at −80° C. for purification later.

Step ③, Purification of a Murine Monoclonal Antibody Targeted to Human TF:

The ascites cryopreserved in Step ① was thawed on ice, and was dialyzed with PBS at 4° C. overnight after filtration through a 0.45 µm filter. Finally, the antibody was purified by FPLC technique, subjected to ultrafiltration, concentrated to the desired concentration, sub-packaged and cryopreserved at −80° C. for further use.

Step ④, Determination of the Bioactivity and Targeting Specificity of a Murine Monoclonal Antibody Targeted to Human TF:

After preliminary screening, about 30 hybridoma cells were selected for secondary limiting dilution cloning, and then 6 antibodies were selected for large-scale expression and purification. Each antibody was determined at a concentration of 10 µg/mL by flow cytometry for its affinity for human breast cancer cell MDA-MB-231, human pancreatic cancer cell BxPC-3 and murine melanoma cell B16-F10.

The result as shown in FIG. 1 indicated that the tested antibodies could specifically bind to human TF (MDA-MB-231 and BxPC-3 cells) without specifically binding to murine TF (B16-F10 cells), wherein TF-mAb-SC1 had a higher affinity for human TF than the other 5 antibodies.

Figure 2:
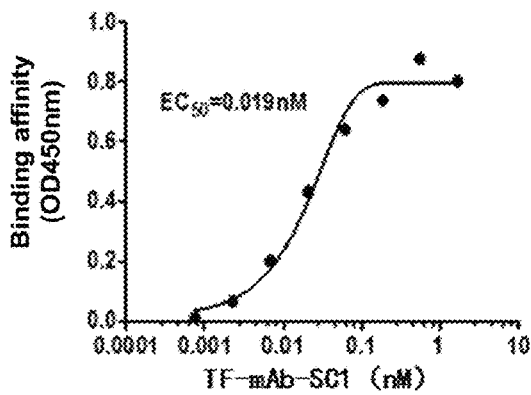
FIG. 2 shows the binding affinity of TF-mAb-SC1 to the extracellular domain protein of TF as determined by ELISA.

The antigen (the extracellular domain protein of TF) was diluted to 0.5 μg/mL with a coating solution, and was used to coat an ELISA plate overnight, at 100 μL/well and 4° C. The excessive antigen was removed by washing. The plate was blocked with 2% BSA at room temperature for 2 h, and then each of the 3-fold serial diluted monoclonal antibodies was added at 100 μL/well, and was incubated for 2 h at room temperature. The unbound antibodies were removed by washing, and an appropriate concentration of horseradish peroxidase-labeled anti-mouse secondary antibody was added at 100 μL/well, and incubated for 1 h at room temperature. The unbound secondary antibody was removed by washing, TMB chromogenic solution was added, and the color was developed to an appropriate color depth. 2M $H_2SO_4$ was added at 50 μL/well, to stop the chromogenic reaction, the absorbance at 450 nm was then determined, and the data was analyzed. As shown in FIG. 2, TF-mAb-SC1 had a strong affinity to the extracellular domain protein of TF, and had an $EC_{50}$ of about 0.019 nM.

Meanwhile, $3\times10^5$ pancreatic cancer cells BxPC-3 were spread on a 12-well plate. 12 h later, the cells were washed with sterile PBS for 3 times, and then starved at 37° C. for 4 h in a 5% $CO_2$ incubator after the addition of a serum-free medium. Each monoclonal antibody was then subjected to 3-fold gradient dilution and incubated with BxPC-3 in an incubator for 1 h, followed by activation of the PAR2 intracellular signal pathway with 25 nM FVIIa in BxPC-3. After interaction for 15 min at 37° C., the cells were washed with pre-cooled PBS once, the proteins in the cells were collected on ice, and the effect of TF-mAb-SC1 on the phosphorylation level of downstream MAPK/ERK was identified by Western blot, wherein only FVIIa stimulation was performed, and the cells, which were not incubated with the monoclonal antibody, were used as positive control. It was designated as Veh, when only solvent was contained and no antibody was added. The effect of said 6 antibodies on the TF-PAR2 intracellular signal pathway in BxPC-3 was determined by Western blot.

Figure 3:
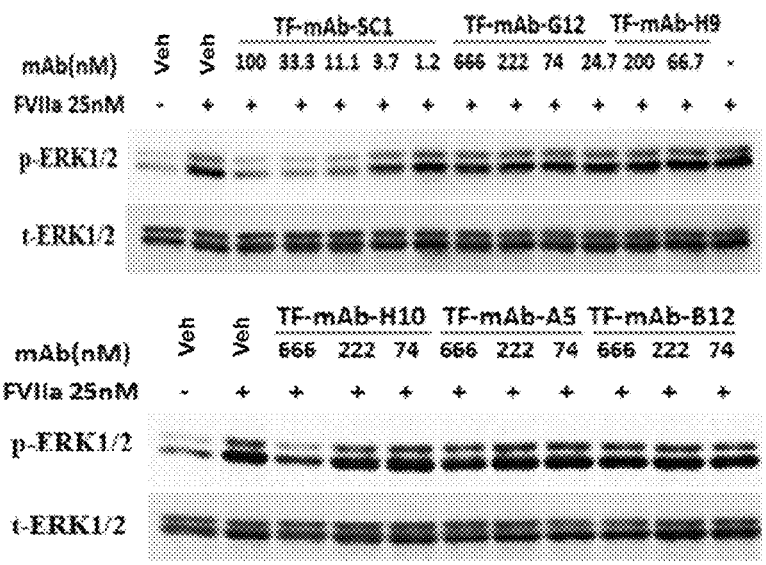
FIG. 3 shows the inhibitory effect of a series of original monoclonal antibodies on the TF-PAR2 intracellular signal pathway in BxPC-3 as determined by Western blot.

The result as shown in FIG. 3 indicated that only TF-mAb-SC1 could significantly inhibit the phosphorylation level of downstream MAPK/ERK with certain degree of dose-dependency.

Since TF-mAb-SC1 exhibited a very high specificity, a very high affinity and a significant inhibitory effect on the phosphorylation level of MAPK/ERK, it was selected for sequencing and subsequent studies.

By conventional sequencing and analysis according to Kabat database, the following sequence information was obtained:

The amino acid sequences of the CDRs of the heavy chain variable region were:

SEQ ID No: 1:
SYWMN;

SEQ ID No: 2:
MIYPADSETRLNQKFKD;

SEQ ID No: 3:
EDYGSSDY.

The complete VH amino acid sequence was as set forth in SEQ ID NO: 7.

(SEQ ID NO: 7)
QVQLQQPGAELVRPGASVKLSCKASGYSFISYWMNWVKQRPGQGLEWI

GMIYPADSETRLNQKFKDKATLTVDKSSSTAYMQLSSPTSEDSAVYYC

AREDYGSSDYWGQGTTLTVSS

The amino acid sequences of the CDRs of the light chain variable region were:

SEQ ID No: 4:
SASSSVSYMN;

SEQ ID No: 5:
GISNLAS;

SEQ ID No: 6:
QQKSSFPWT.

The complete VL amino acid sequence was as set forth in SEQ ID NO: 8:

(SEQ ID NO: 8)
EILLTQSPAIIAASPGEKVTITCSASSSVSYMNWYLQKPGSSPKIWIY

GISNLASGVPARFSGSGSGTSFSFTINSMETEDVATYYCQQKSSFPWT

FGGGTKLEIK

Example 2 Preparation of a Human-Mouse Chimeric Antibody

A human-mouse chimeric antibody was constructed based on the highly active and specific murine TF-mAb-SC1 obtained.

By analysis according to the relevant database, the amino acid sequences of the CDRs of the heavy chain variable region were:

SEQ ID No: 18: MIYPXDSETRLNXKFKD (X is any one selected from the group consisting of A, D, E, Q, and Y)

SEQ ID No: 19: GYSFXSYWMN (X is any one selected from the group consisting of A, I, Y, Q, and W)

SEQ ID No: 20: AREDYGXSDY (X is any one selected from the group consisting of S, P, G, D, M, and N).

By analysis according to the relevant database, the amino acid sequences of the CDRs of the light chain variable region were:

SEQ ID No: 21: QQXSSFXWT (X is any one selected from the group consisting of S, P, K, G, and H);

SEQ ID No: 22: SASSXVSYMN (X is any one selected from the group consisting of A, P, D, and S);

SEQ ID No: 23: GXSNLAS (X is any one selected from the group consisting of P, D, I, and S).

Figure 4A:
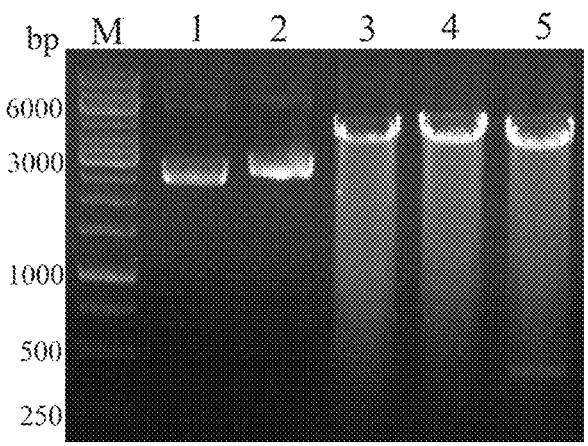
FIG. 4A shows the identification result of the expression plasmid of the heavy chain variable region by single enzyme digestion and double enzyme digestion.
Figure 4B:
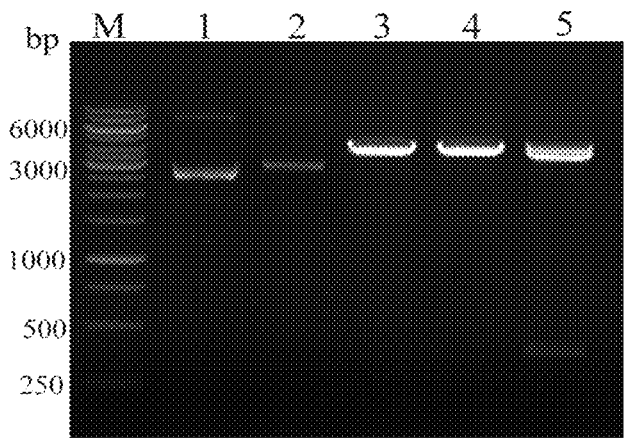
FIG. 4B shows the identification result of the expression plasmid of the light chain variable region by single enzyme digestion and double enzyme digestion.

Primers were designed to introduce EcoR I and Nhe I in the heavy chain variable region, and to introduce the Age I and BsiW I restriction endonuclease sites in the light chain variable region, and then the variable region sequences of the antibody heavy and light chain obtained above were separately cloned into vectors containing the heavy chain constant region and the Kappa chain constant region of human IgG1. After confirmation by identification (FIG. 4A showed the identification result of the enzyme digestion of heavy chain, and FIG. 4B showed the identification result of the enzyme digestion of light chain, wherein Sample 1 was the blank vector of the corresponding heavy/light chain, Sample 2 was a vector into which the heavy chain/light chain variable region was cloned, Samples 3 and 4 were the samples after single enzyme digestion, and Sample 5 was a sample after double enzyme digestion), the constructed chimeric antibody was expressed and purified by using transfection technique and a mammalian expression system (CHO-S or HEK-293 cells), and the human-mouse chimeric antibody obtained was designated as TF-mAb-Ch.

Example 3 Determination of the Binding Affinity of TF-mAb-SC1 for TF-Positive Tumor Cells In this experiment, triple-negative breast cancer cell MDA-MB-231, pancreatic cancer cell BxPC-3, malignant glioma cell U87MG and non-small cell lung cancer cell H1975, which had TF highly expressed on the cell surface, were used as target cells; and 100 µL TF-mAb-SC1, which was diluted from 333.33 nM to 0.15 nM by 3-fold serial dilution, was used as a primary antibody, and was mixed homogeneously with $3\times10^5$ MDA-MB-231 or BxPC-3 suspended in 100 µL RPMI-1640 serum-free medium, respectively; or 100 µL TF-mAb-SC1, which was diluted from 66.67 nM to 0.03 nM by 3-fold serial dilution, was used as a primary antibody, and was mixed homogeneously with $3\times10^5$ U87MG suspended in 100 µL MEM serum-free medium; or 100 µL 33.33 nM and 3.33 nM TF-mAb-SC1 as a primary antibody was mixed with $3\times10^5$ H1975 suspended in 100 µL RPMI-1640 serum-free medium, and then incubated at 4° C. for 1 h. The cells were washed with PBS twice to remove the unbound primary antibody, and the target cells were incubated with 200 µL PE-labeled secondary antibody (2 µg/mL) at 4° C. for 30 min. The cells were washed with PBS twice to remove the unbound secondary antibody, and finally the cells were re-suspended in 400 µL PBS. TF-mAb-SC1 was determined by flow cytometry for its binding affinity for the corresponding cell surface TF.

Figure 5A:
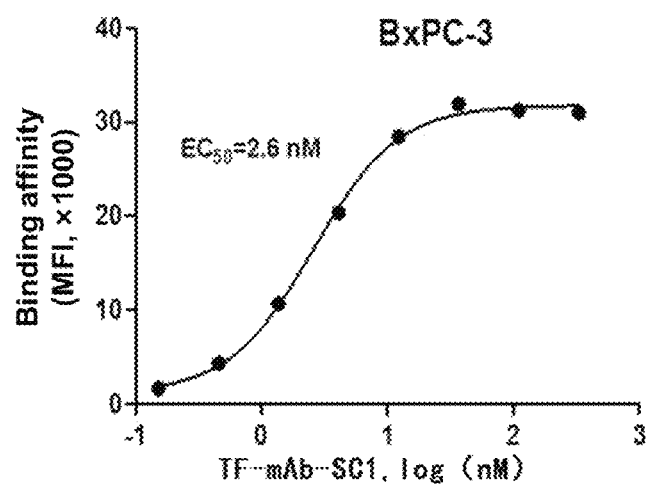
FIG. 5A shows the result on the binding affinity to BxPC-3 cells.
Figure 5B:
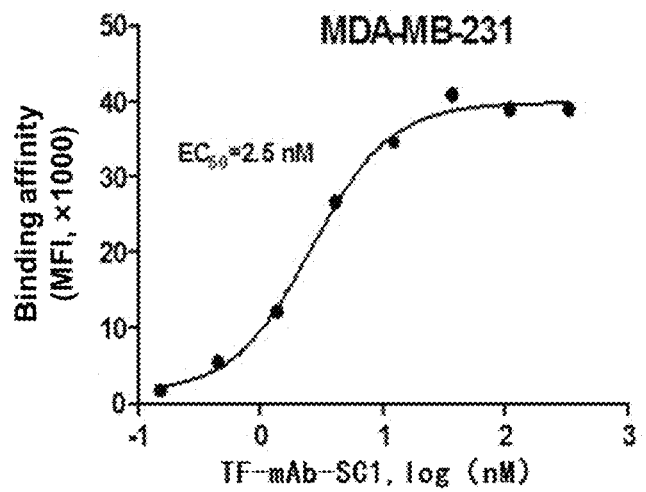
FIG. 5B shows the result on the binding affinity to MDA-MB-231 cells.
Figure 5C:
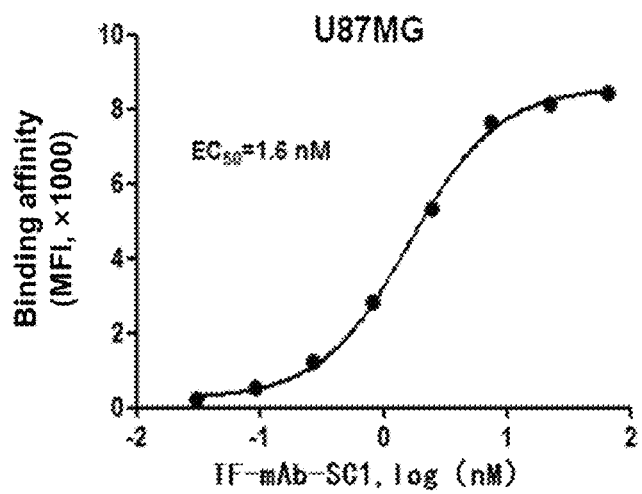
FIG. 5C shows the result on the binding affinity to U87MG cells.
Figure 5D:
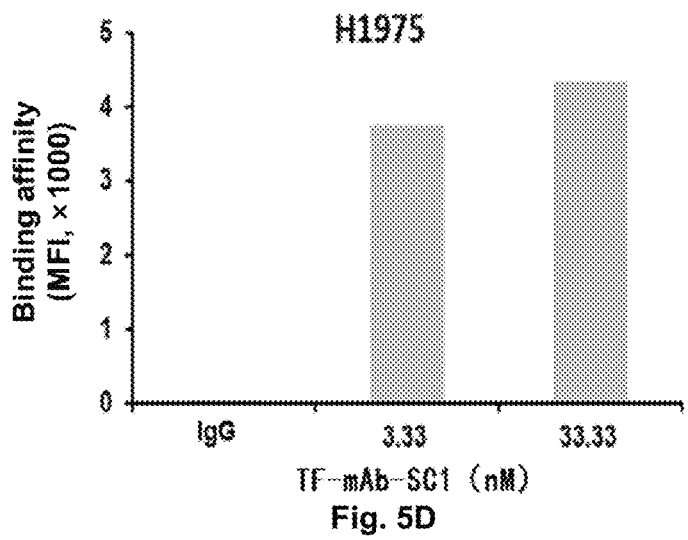
FIG. 5D shows the result on the binding affinity to H1975 cells.

As shown in FIG. 5, TF-mAb-SC1 had a good binding affinity to BxPC-3, MDA-MB-231 and U87MG cells, and had an $EC_{50}$ of 2.6 nM (FIG. 5A), 2.5 nM (FIG. 5B) and 1.6 nM (FIG. 5C), respectively; and FIG. 5D showed that TF-mAb-SC1 also had a good binding affinity to H1975 cells.

This indicated that the monoclonal antibody in the Example could use human TF as target.

Example 4 Effect of TF-mAb-SC1 on the TF-PAR2 Intracellular Signal Pathway $3\times10^5$ pancreatic cancer cells (BxPC-3) were plated in a 12-well plate. 12 h later, the cells were washed with sterile PBS for 3 times, and then were starved at 37° C. for 4 h in a 5% $CO_2$ incubator after the addition of a serum-free medium. TF-mAb-SC1 was then diluted from 100 nM to 1.2 nM by 3-fold serial dilution, and incubated with BxPC-3 cells for 1 h in the incubator, followed by activation of the PAR2 intracellular signal pathway with 25 nM FVIIa in BxPC-3 cells. After interaction at 37° C. for 15 min, the cells were washed with pre-cooled PBS once, and the cellular proteins were collected on ice. The effect of TF-mAb-SC1 on the phosphorylation level of downstream MAPK/ERK was identified by Western blot, wherein FVIIa stimulation alone without TF-mAb-SC1 treatment was used as a control.

Figure 6:
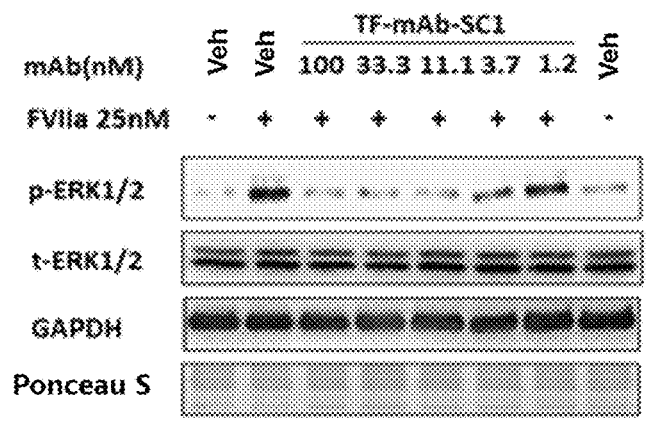
FIG. 6 shows the effect of TF-mAb-SC1 on the FVIIa-activated TF-PAR2 intracellular signal pathway in BxPC-3 cells.

The result as shown in FIG. 6 indicated that TF-mAb-SC1 potently and dose dependently inhibited the phosphorylation level of downstream MAPK/ERK signaling.

Example 5 Determination of the Anticoagulant Activity of TF-mAb-SC1

100 nM TF-mAb-SC1 was serially diluted to 1.5625 nM (with a final volume of 50 µL), and was separately incubated with $3\times10^4$ MDA-MB-231 and BxPC-3 cells suspended in 50 µL Hanks Balanced Salt Solution (HBSS) containing 5 mM $CaCl_2$, for 15 min at room temperature. 50 µL citrate human plasma was then added, and the resultant mixture was rapidly mixed homogeneously. The absorbance at 405 nm was determined every 15 s within the next 2 h, so as to calculate the anticoagulant effect on the coagulation initiated by TF on the cell surface.

Figure 7A:
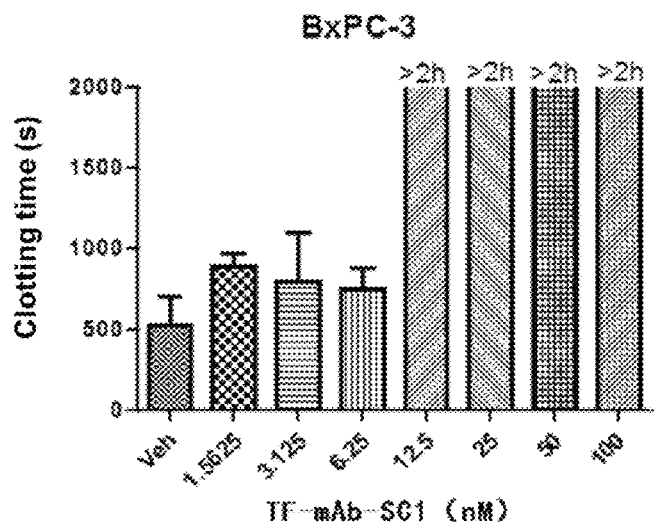
FIG. 7 shows the activity of TF-mAb-SC1 for inhibiting the coagulation initiated by TF derived from BxPC-3 cells (FIG. 7A) and MDA-MB-231 cells (FIG. 7B).
Figure 7B:
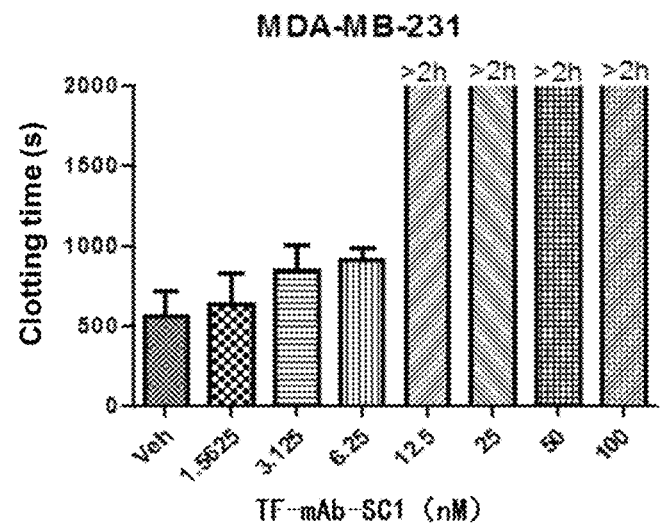

In FIG. 7, the ordinate represented the time at achievement of the maximum coagulation rate, the abscissa represented the concentration of TF-mAb-SC1, and TF on the cell surface of BxPC-3 (FIG. 7A) and MDA-MB-231 (FIG. 7B) was used as the source of TF. The experimental results showed that TF-mAb-SC1 had significant anticoagulant activity at a concentration of ≤12.5 nM.

Example 6 Determination of the Activity of TF-mAb-SC1 for Inhibiting the FXa Production 100 nM TF-mAb-SC1 was serially diluted to 1.5625 nM (with a final volume of 50 µL), and was separately incubated with $1.5\times10^4$ BxPC-3 and MDA-MB-231 cells suspended in 50 µL HBSS (containing 3 nM FVIIa), for 20 min at room temperature under shaking. 50 µL FX (at a final concentration of 50 nM) was then added to initiate the reaction, and 5 min later, 1M EDTA (25 µL) was added to stop the reaction. Later, 3 mM S2765 (25 µL) was added, and the resultant mixture was rapidly mixed homogeneously. The kinetic reaction curve was measured every 15 s with the next 60 min so as to calculate the activity of inhibiting FXa production.

Figure 8A:
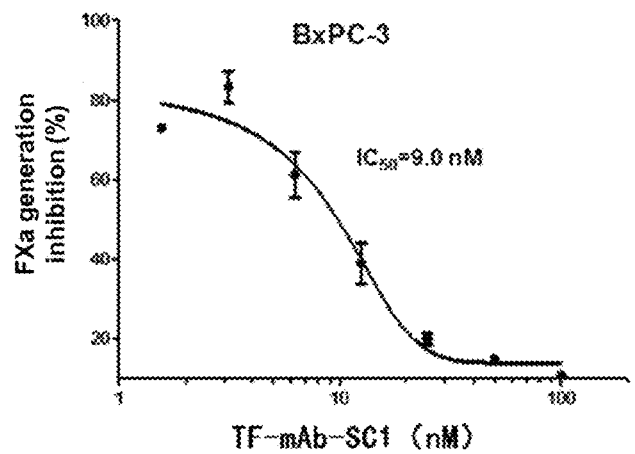
FIG. 8 shows the result on the activity of TF-mAb-SC1 for inhibiting the FXa production induced by TF derived from BxPC-3 cells (FIG. 8A) and MDA-MB-231 cells (FIG. 8B).
Figure 8B:
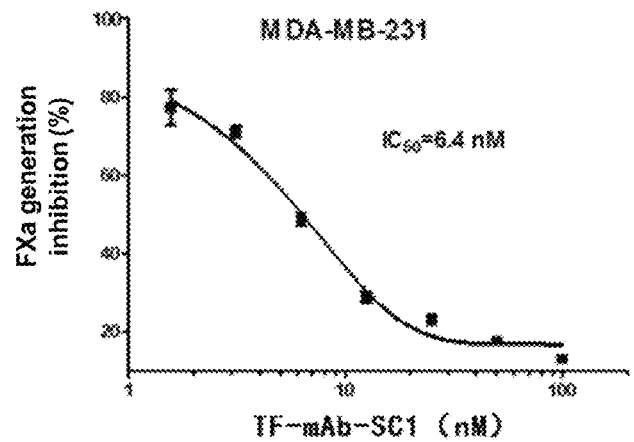

As shown in FIG. 8, TF-mAb-SC1 showed a good activity of inhibiting FXa production, and had an $IC_{50}$ of 9.0 nM (FIG. 8A), and an $IC_{50}$ of 6.4 nM (FIG. 8B).

Example 7 Evaluation of TF-mAb-SC1 for its Activity of Inhibiting Tumor Growth In Vivo Nude mice were randomly divided into two groups, with 10 mice for each group. Firstly, tumor cells ($1\times10^7$ BxPC-3 or $5\times10^6$ U87MG or $2.5\times10^6$ HCC1806) were mixed with 100 µg TF-mAb-SC1 at room temperature. After incubation at room temperature for 30 min, 6-week-old immunodeficient female mice (Balb/c nude mice) were inoculated with the resultant mixture at the back or mammary fatty pad so as to observe the inhibitory effect on subcutaneous tumor growth of BxPC-3. The other group of mice, which were inoculated with normal mouse IgG (marked as IgG in the figure), were used as as control. The nude mice were measured for their body weight and tumor size periodically, the tumor growth curves were plotted, and the activity was evaluated.

Figure 9:
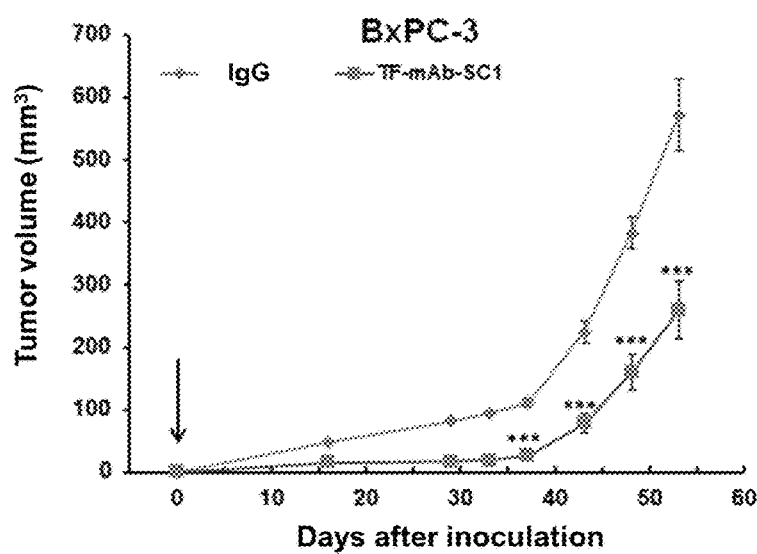
FIG. 9 shows the activity of TF-mAb-SC1 for inhibiting subcutaneous BxPC-3 xenograft tumor growth in nude mouse (the arrow indicates the time of starting administration).

As shown in FIG. 9, as compared with lgG, TF-mAb-SC1 had a significant inhibitory effect on BxPC-3 subcutaneous xenograft tumor growth, and had a maximum inhibition rate of up to 80%, and when the experiment was finished, the inhibition rate of tumor growth was 55%.

Figure 10:
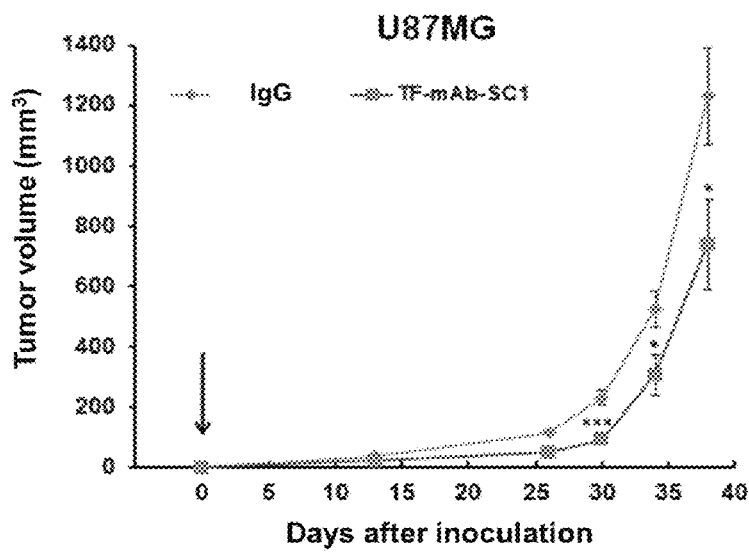
FIG. 10 shows the result on the activity of TF-mAb-SC1 for inhibiting subcutaneous U87MG xenograft tumor growth in nude mouse (the arrow indicates the time of starting administration).

As shown in FIG. 10, as compared with lgG, TF-mAb-SC1 had a significant inhibitory effect on U87MG subcutaneous xenograft tumor growth, and had a maximum inhibition rate of up to 60%, and when the experiment was finished, the inhibition rate of tumor growth was 36%.

Figure 11:
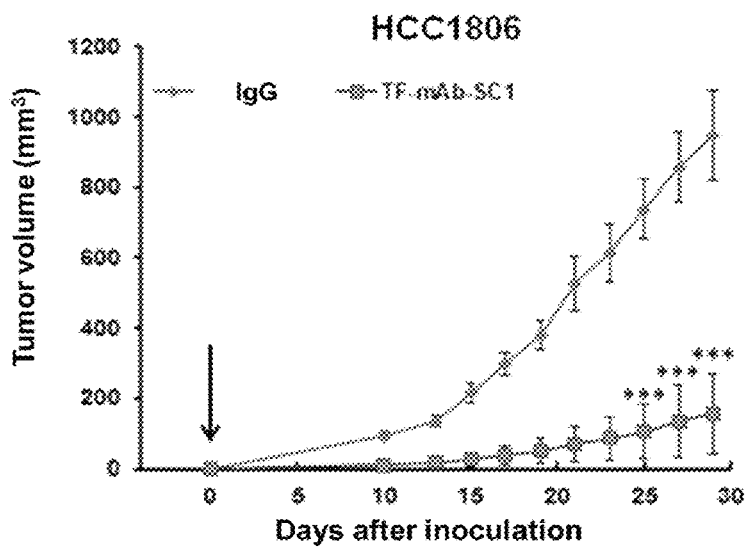
FIG. 11 shows the result on the activity of TF-mAb-SC1 for inhibiting in situ HCC1806 xenograft tumor growth (the arrow indicates the time of starting administration).

As shown in FIG. 11, as compared with lgG, TF-mAb-SC1 could significantly inhibit HCC1806 subcutaneous xenograft tumor growth, and had a maximum inhibition rate of >90%, and when the experiment was finished, the inhibition rate of tumor growth was up to 83%.

Example 8 Significant Inhibition of Accumulation of Tumor Matrix Collagen by TF-mAb-SC1

BxPC-3 tumors from Example 7 were collected, and were fixed in 4% neutral formaldehyde, followed by paraffin embedding and section, routinely dewaxing to water and Masson staining. For each stained sample, 5 to 10 fields were taken at 100× magnification (100 μm in the legend) and were statistically analyzed.

Figure 12:
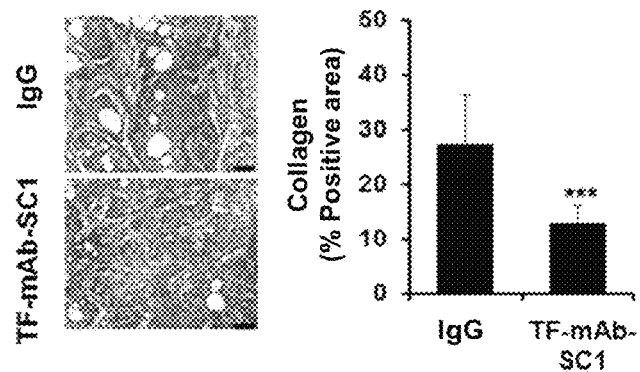
FIG. 12 shows the activity of TF-mAb-SC1 for inhibiting accumulation of BxPC-3 tumor matrix collagen and the result of statistic analysis using Image-pro plus.

The result shown in FIG. 12 indicated that TF-mAb-SC1 could significantly inhibit the accumulation of tumor matrix collagen (blue area), which may contribute to tumor growth inhibition, wherein the right panel showed the result of statistical analysis using Image-pro plus.

Example 9 Significant Reduction of the Lumen Area of Tumor Blood Vessel by TF-mAb-SC1

BxPC-3 tumors from Example 7 were collected, and were fixed in 4% neutral formaldehyde, followed by paraffin embedding and section, routinely dewaxing to water and CD31 immunohistochemical staining. For each immunohistochemically stained sample, 5 to 10 fields were taken at 200× magnification (50 μm in the legend) and statistically analyzed.

Figure 13:
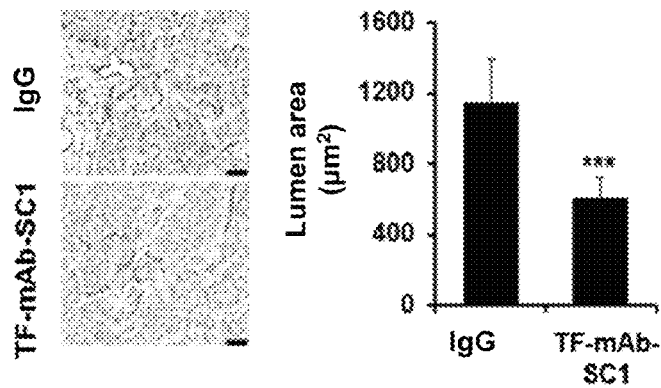
FIG. 13 shows the activity of TF-mAb-SC1 for reducing the lumen area of BxPC-3 tumor blood vessel and the statistic result thereof.

The result shown in FIG. 13 indicated that TF-mAb-SC1 could significantly reduce the lumen area of tumor blood vessel, wherein the right figure showed the statistic result of the lumen area of blood vessel.

Example 10 Determination of TF-mAb-SC1 for its Activity of Inhibiting Migration of Tumor Cells The effect of TF-mAb on tumor cell migration levels was evaluated in vitro using the transwell chamber system: $1×10^5$ MDA-MB-231 or $8×10^4$ BxPC-3 cells were separately mixed with a certain concentration of TF-mAb-SC1 (100 nM, 33.3 nM or 11.1 nM) or mouse IgG (marked as IgG in the figure) in 200 μL serum-free medium; the resultant mixture was added to the upper chamber, and 600 μL complete medium containing 10% FBS was added to the bottom chamber; the cells were incubated at 37° C. in a 5% $CO_2$ incubator; 8 h later, the cells on the upper surface of the chamber membrane were wiped off with a wet cotton swab. The cells on the lower surface of the membrane were fixed with 95% ethanol for 30 min, and then were stained in 0.2% crystal violet for 30 min, and washed with distilled water to remove the excessive crystal violet. After drying at room temperature, five representative fields were randomly selected under a microscope, and the number of cells migrating to the lower surface of the chamber membrane was counted and analyzed. In this experiment, both the TF knocked-out cells (sh-TF) and the corresponding vector control cells (sh-NT) were used to further confirm the activity of TF-mAb-SC1 for inhibiting migration of tumor cells.

Figure 14A:
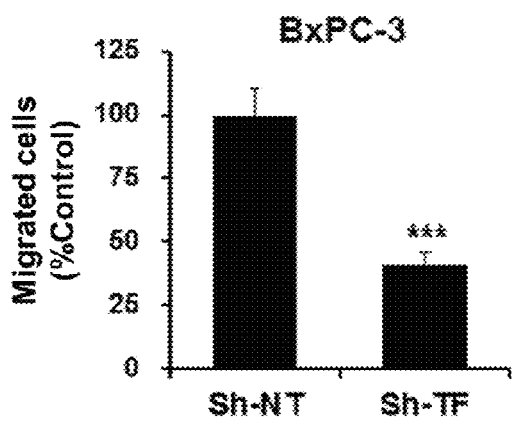
FIG. 14 shows the determination of the migration ability of MDA-MB-231 cells (FIG. 14A) and BxPC-3 cells (FIG. 14B) under the condition where TF gene is knocked out.
Figure 14B:
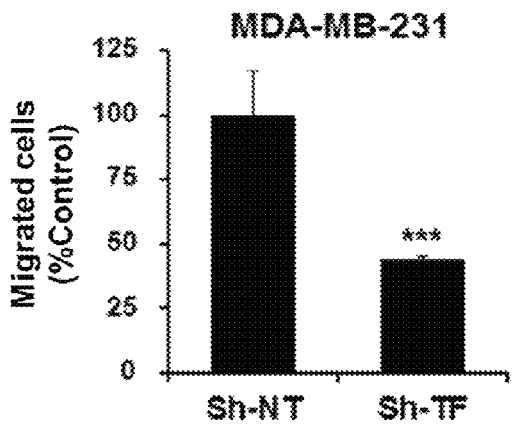

As shown in FIG. 14, the migration of MDA-MB-231 (FIG. 14A) and BxPC-3 (FIG. 14B) cells was significantly inhibited by knocking out TF gene.

Figure 15A:
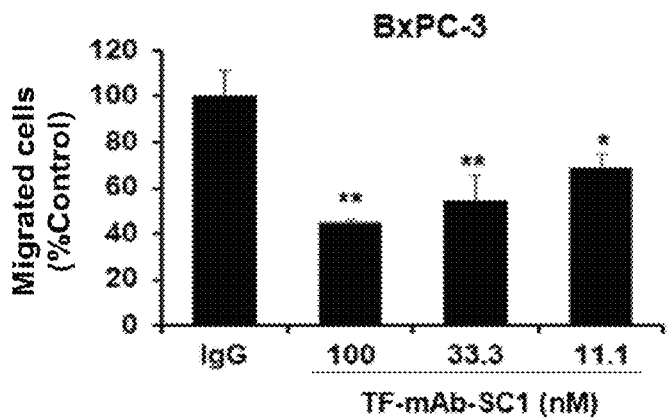
FIG. 15 shows the determination of the activity of TF-mAb-SC1 for inhibiting the migration ability of MDA-MB-231 cells (FIG. 15A) and BxPC-3 cells (FIG. 15B).
Figure 15B:
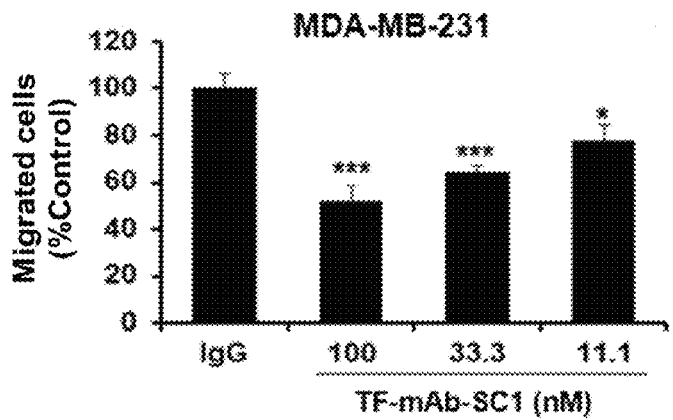

As shown in FIG. 15, TF-mAb-SC1 could significantly inhibit the migration level of MDA-MB-231 (FIG. 15A) and BxPC-3 (FIG. 15B) cells in a concentration-dependent manner.

The result suggested that the migration of tumor cells could be effectively inhibited by inhibiting TF.

Example 11 Significant Inhibition of In Vivo Hematogenous Metastasis of Tumor Cells by TF-mAb-SC1

The effect of TF-mAb-SC1 on the migration level of tumor cells was evaluated in vivo using an experimental model of hematogenous metastasis: $2×10^6$ luciferase-labeled MDA-MB-231 cells (MDA-MB-231-luc) were mixed with 100 μg TF-mAb-SC1 or mouse IgG in 200 μL PBS, were incubated on ice for 20 min, and then were slowly injected into the tail vein of 6-week-old Balb/c female nude mice; 4 h later, the nude mice were anesthetized, and a solution of D-luciferin potassium salt in PBS was intraperitoneally injected into the nude mice at a dose of 150 mg/kg; 6 min later, the mice were exposed to a small-animal in vivo imaging system (IVIS SPECTRUM) for 1 min, and the fluorescence intensity was measured; and statistical analysis was carried out, with 5 nude mice for each group.

Figure 16:
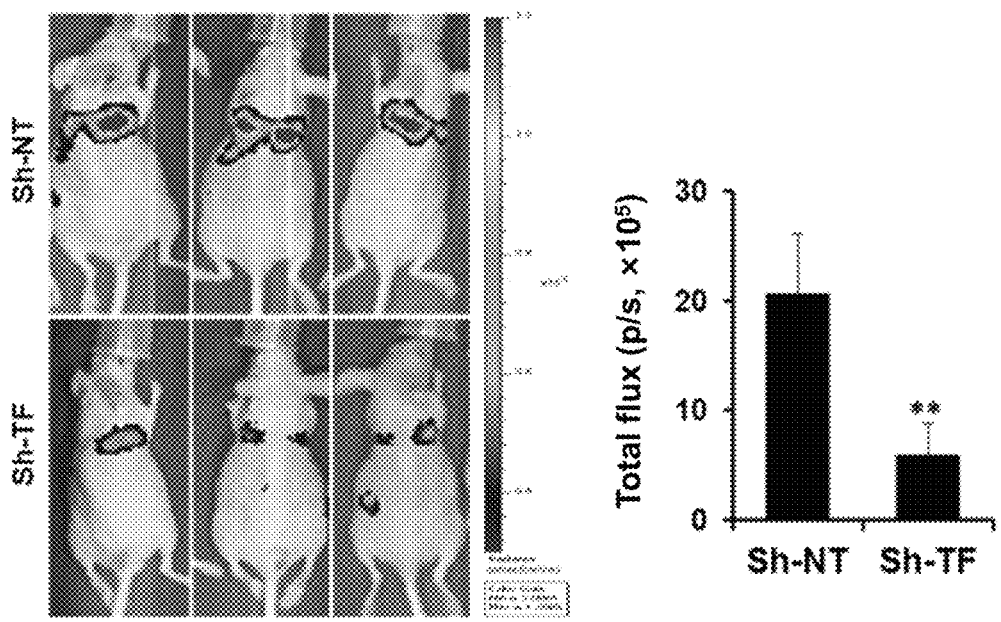
FIG. 16 shows the determination of the hematogenous migration ability of MDA-MB-231-luc cells in mice after the TF gene is knocked out, and the statistic result of the fluorescence intensity thereof.

As shown in FIG. 16, the knockout of TF gene could significantly inhibit the hematogenous migration ability of MDA-MB-231-luc. Similarly, as shown in FIG. 17, TF-mAb-SC1 could also significantly inhibit the hematopoietic migration ability of MDA-MB-231-luc cells, wherein the right figure showed the statistical result of the fluorescence intensity of the cells migrated to lung.

$3×10^6$ MDA-MB-231 cells were mixed with 100 μg TF-mAb-SC1 or IgG in 200 μL PBS, incubated on ice for 20 min, and then slowly injected into the tail vein of 6-week-old female SCID Beige mice. Six weeks later, the mice were sacrificed, and the lungs were taken and fixed in Bouin's solution, and then photographed and weighed. The number of metastatic foci on each lung was recorded, with 7 mice for each group.

The result shown in FIG. 18 indicated that TF-mAb-SC1 significantly inhibited the formation and growth of tumor metastatic foci on mouse lung.

Example 12 Rapid and Efficient Internalization of TF-mAb-SC1 to Lysosomes

MDA-MB-231 cells with a density of 50% were plated in a culture dish specific for use in a laser confocal microscope. About 16 h later, 10 μg/mL TF-mAb-SC1 was added, and the cells were incubated at 37° C. or 4° C. for 1 h, washed with pre-warmed PBS for three times to remove the antibody not bound to the cells, and then fixed with 4% paraformaldehyde for 30 min at room temperature. After washing with PBS for three times, the cells were incubated with Lamp-2 (rabbit anti-human) antibody at 37° C. for 1 h so as to label the position of the lysosomes, the unbound antibodies were removed by washing with PBS. After incubation with Alexa Fluor 594-labeled donkey anti-mouse secondary antibody and Alexa Fluor 488-labeled donkey anti-rabbit secondary antibody at 37° C. for 30 min, the unbound antibodies were removed by washing, the nucleus position was labeled by DAPI staining, and then the internalization of antibodies were observed under a laser confocal microscope.

As shown in FIG. 19, TF-mAb-SC1 could be internalized to lysosomes.

Example 13 Determination of the Bioactivity of TF-mAb-Ch

Figure 20:
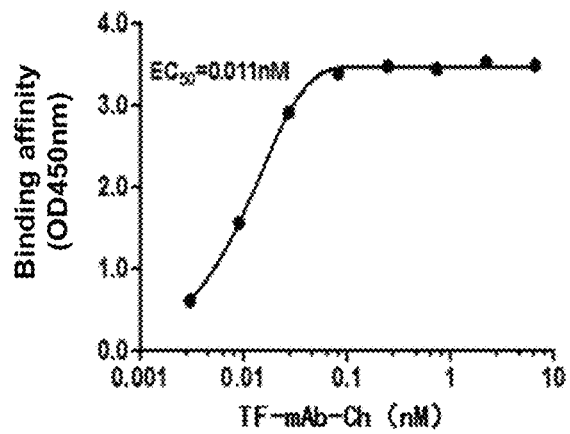
FIG. 20 shows the binding affinity of the chimeric antibody TF-mAb-Ch to the extracellular domain protein of TF as determined by ELISA.

The experimental method refers to Step ④ in Example 1.
The result shown in FIG. 20 indicated that TF-mAb-Ch had a strong affinity for the extracellular domain protein of TF, and had an $EC_{50}$ of approximately 0.011 nM.

Figure 21A:
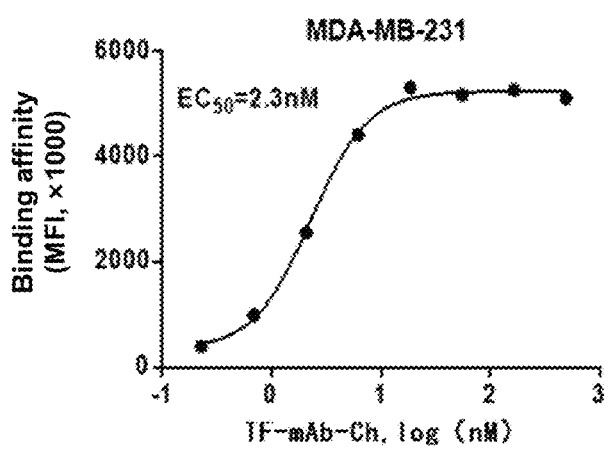
FIG. 21A shows the binding affinity of TF-mAb-Ch to the TF-positive tumor cell MDA-MB-231.
Figure 21B:
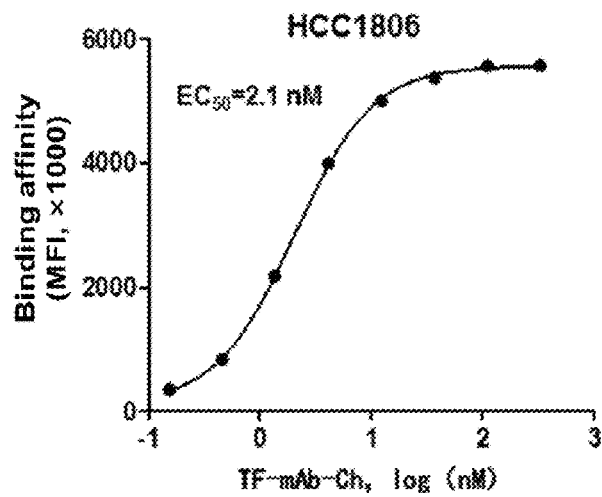
FIG. 21B shows the result on the binding affinity of TF-mAb-Ch to the TF-positive tumor cell HCC1806.

Example 14 Determination of the Binding Affinity of TF-mAb-Ch for TF-Positive Tumor Cells The experimental method is by referring to Example 3.
The result showed that TF-mAb-Ch had a good binding affinity for both MDA-MB-231 (FIG. 21A) and HCC1806 (FIG. 21B) cells, and had an $EC_{50}$ of 2.3 nM and 2.1 nM, respectively.

Example 15 Effect of TF-mAb-Ch on the TF-PAR2 Intracellular Signal Pathway

Figure 22:
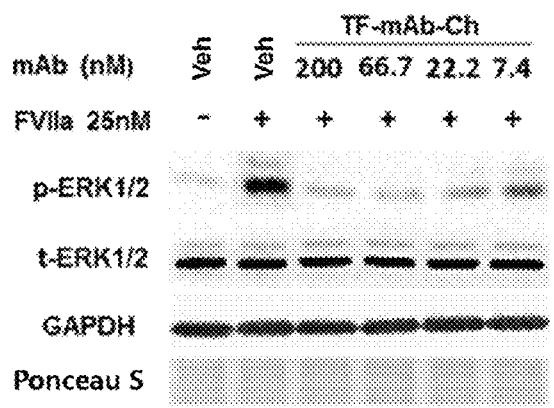
FIG. 22 shows the activity of TF-mAb-Ch for inhibiting the TF-PAR2 intracellular signal pathway in BxPC-3 cells.

The experimental method is by referring to Example 4.
The result shown in FIG. 22 indicated that TF-mAb-Ch inhibited the FVIIa-induced phosphorylation level of MAPK/ERK in a concentration-dependent manner.

Example 16 Rapid and Efficient Internalization of TF-mAb-Ch to Lysosomes

Figure 23:
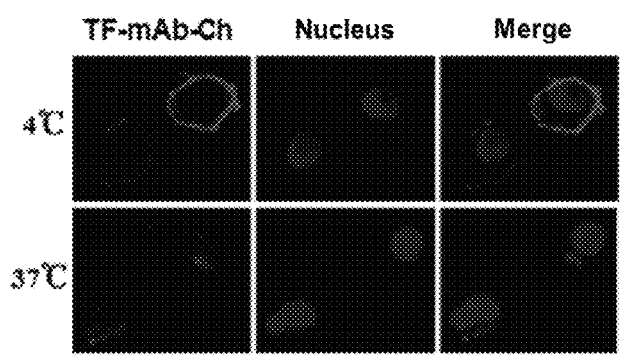
FIG. 23 shows the result on internalization of TF-mAb-Ch to lysosome by MDA-MB-231 cell.

The experimental method is by referring to Example 12.
The result shown in FIG. 23 indicated that TF-mAb-Ch could be internalized to lysosomes.

The experiments above suggested that since the TF-mAb antibody according to the present invention could be easily internalized, it was suitable for development into an antibody-drug conjugate (ADC) and for application in the treatment of high TF expression-associated tumors.

Example 17 Humanization of TF-mAb-SC1 and Determination of Activity

By reference to the sequences of the heavy chain variable region (SEQ ID NO: 7) and the light chain variable region (SEQ ID NO: 8) of the antibody TF-mAb-SC1, the humanized template, which matched the non-CDR regions best, was selected in the Germline database. The CDR regions of the murine antibody TF-mAb-SC1 were then grafted to the humanized template selected, so as to replace the CDR regions of the humanized template, followed by recombination with the IgG1/kappa constant region. Meanwhile, based on the three-dimensional structure of the murine antibody, back mutation was performed to the residues that were directly interacted with the CDR regions, and to the residues that had a important effect on the conformation of VL and VH, thereby obtaining 5 humanized heavy chain variable regions (SEQ ID NO: 9, SEQ ID NO: 10, SEQ ID NO: 11, SEQ ID NO: 12, and SEQ ID NO: 13) and 4 humanized light chain variable regions (SEQ ID NO: 14, SEQ ID NO: 15, SEQ ID NO: 16, and SEQ ID NO: 17).

| SEQ ID NO: | Sequence | Variable region |
|---|---|---|
| 9 | EVQLVQSGAEVKKPGESLKISCKGSGYSFTSYWMNWVRQMPGKGLEWMGMIYPADSETRLNQKFKDQATLSVDKSISTAYLQWSSLKASDTAMYYCAREDYGSSDYWGQGTTVTVSS | VH |
| 10 | EVQLVQSGAEVKKPGESLKISCKGSGYSFTSYWMNWVRQMPGKGLEWMGMIYPADSETRLNQKFKDKATLSVDKSISTAYLQWSSLKASDTAMYYCAREDYGSSDYWGQGTTVTVSS | VH |
| 11 | EVQLVQSGAEVKKPGESLKISCKGSGYSFTSYWMNWVKQMPGKGLEWMGMIYPADSETRLNQKFKDKATLSVDKSISTAYLQWSSLKASDTAMYYCAREDYGSSDYWGQGTTVTVSS | VH |
| 12 | QVQLVQSGAEVKKPGASVKVSCKASGYSFISYWMNWVRQAPGQGLEWIGMIYPADSETRLNQKFKDRATLTVDKSTSTAYMELSSLRSEDTAVYYCAREDYGSSDYWGQGTTVTVSS | VH |
| 13 | QVQLVQSGSELKKPGASVKVSCKASGYSFISYWMNWVRQAPGQGLEWIGMIYPADSETRLNQKFKDRAVLSVDKSVSTAYLQICSLKAEDTAVYYCAREDYGSSDYWGQGTTVTVSS | VH |
| 14 | EIVLTQSPATLSLSPGERATLSCSASSSVSYMNWYQQKPGQAPRIWIYGISNLASGIPARFSGSGSGTDFTLTISSLEPEDFAVYYCQQKSSFPWTFGGGTKVEIK | VL |
| 15 | EIVLTQSPATLSLSPGERATLSCSASSSVSYMNWYQQKPGQSPRIWIYGISNLASGVPARFSGSGSGTDFTLTISSLEPEDFAVYYCQQKSSFPWTFGGGTKVEIK | VL |
| 16 | DIQLTQSPSSLSASVGDRVTITCSASSSVSYMNWYQQKPGKSPKIWIYGISNLASGVPSRFSGSGSGTDFTLTISSLQPEDFATYYCQQKSSFPWTFGGGTKVEIK | VL |
| 17 | EIVLTQSPDFQSVTPKEKVTITCSASSSVSYMNWYQQKPDQSPKIWIYGISNLASGVPSRFSGSGSGTDFTLTINSLEAEDAATYYCQQKSSFPWTFGGGTKVEIK | VL |

Based on the engineered VH and VL, these humanized heavy and light chains were separately expressed in combination to finally obtain 20 humanized antibodies in total, i.e. TF-mAb-H29 to TF-mAb-H48. The corresponding combination of heavy chain and light chain for each antibody was shown in the following table:

| Sequence No. | SEQ ID NO: 9 | SEQ ID NO: 10 | SEQ ID NO: 11 | SEQ ID NO: 12 | SEQ ID NO: 13 |
|---|---|---|---|---|---|
| SEQ ID NO: 14 | TF-mAb-H29 | TF-mAb-H30 | TF-mAb-H31 | TF-mAb-H32 | TF-mAb-H33 |
| SEQ ID NO: 15 | TF-mAb-H34 | TF-mAb-H35 | TF-mAb-H36 | TF-mAb-H37 | TF-mAb-H38 |

| Sequence No. | SEQ ID NO: 9 | SEQ ID NO: 10 | SEQ ID NO: 11 | SEQ ID NO: 12 | SEQ ID NO: 13 |
|---|---|---|---|---|---|
| SEQ ID NO: 16 | TF-mAb-H39 | TF-mAb-H40 | TF-mAb-H41 | TF-mAb-H42 | TF-mAb-H43 |
| SEQ ID NO: 17 | TF-mAb-H44 | TF-mAb-H45 | TF-mAb-H46 | TF-mAb-H47 | TF-mAb-H48 |

Figure 24A:
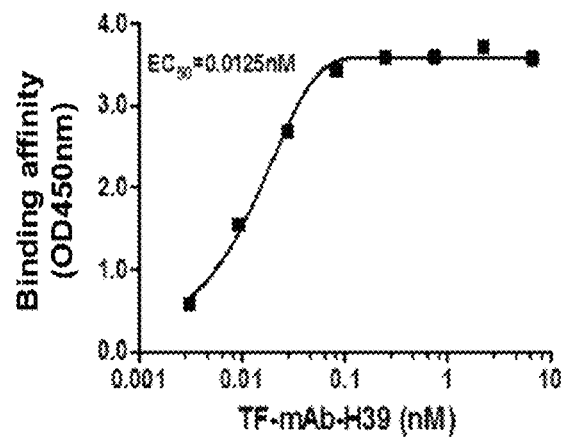
FIG. 24A shows the binding affinity of the humanized antibody TF-mAb-H39 to the extracellular domain protein of TF as determined by ELISA.
Figure 24B:
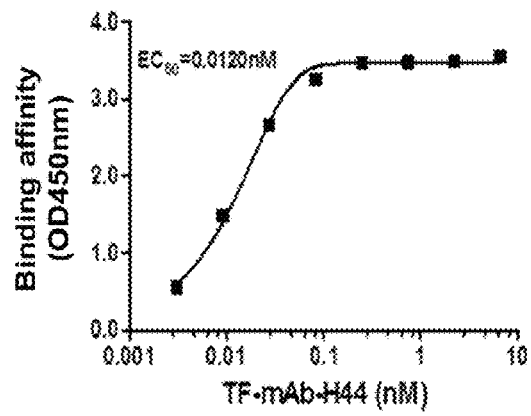
FIG. 24B shows the binding affinity of the humanized antibody TF-mAb-H44 to the extracellular domain protein of TF as determined by ELISA.

Firstly, the 20 humanized antibodies were determined for their affinity for the extracellular domain protein of TF by ELISA binding assay (The experimental method refers to Step ④ of Example 1). The result was shown in Table 1. The binding affinity curves of TF-mAb-H39 and TF-mAb-H44 for the extracellular domain protein of TF were shown in FIG. 24A and FIG. 24B, respectively.

TABLE 1

The binding affinity of humanized antibodies to the extracellular domain protein of TF

| Antibody | $EC_{50}$ (nM) |
|---|---|
| TF-mAb-Ch | 0.0100 |
| TF-mAb-H29 | 0.0178 |
| TF-mAb-H30 | 0.0147 |
| TF-mAb-H31 | 0.0145 |
| TF-mAb-H32 | 0.0168 |
| TF-mAb-H33 | 0.0189 |
| TF-mAb-H34 | 0.0154 |
| TF-mAb-H35 | 0.0105 |
| TF-mAb-H36 | 0.0234 |
| TF-mAb-H37 | 0.0173 |
| TF-mAb-H38 | 0.0178 |
| TF-mAb-H39 | 0.0125 |
| TF-mAb-H40 | 0.0131 |
| TF-mAb-H41 | 0.0134 |
| TF-mAb-H42 | 0.0128 |
| TF-mAb-H43 | 0.0116 |
| TF-mAb-H44 | 0.0120 |
| TF-mAb-H45 | 0.0138 |
| TF-mAb-H46 | 0.0119 |
| TF-mAb-H47 | 0.0130 |
| TF-mAb-H48 | 0.0153 |
| IgG negative control | >6.67 |

These 20 humanized antibodies were determined for their binding affinity for MDA-MB-231 cells at 10 μg/mL and 1 μg/mL by flow cytometry. The experimental method is by referring to Example 3, and the result was shown in Table 2.

TABLE 2

The binding affinity of humanized antibodies to MDA-MB-231;

| | MFI | |
|---|---|---|
| Antibody | 10 μg/mL | 1 μg/mL |
| TF-mAb-Ch | 3544 | 3369 |
| TF-mAb-H29 | 3584 | 2958 |
| TF-mAb-H30 | 3240 | 2930 |
| TF-mAb-H31 | 3468 | 3079 |
| TF-mAb-H32 | 3009 | 2400 |
| TF-mAb-H33 | 2837 | 2420 |
| TF-mAb-H34 | 3272 | 2462 |
| TF-mAb-H35 | 3015 | 2931 |
| TF-mAb-H36 | 3094 | 3037 |
| TF-mAb-H37 | 2989 | 2459 |
| TF-mAb-H38 | 3152 | 2871 |
| TF-mAb-H39 | 3383 | 3177 |
| TF-mAb-H40 | 3311 | 3182 |
| TF-mAb-H41 | 3613 | 3004 |
| TF-mAb-H42 | 3350 | 2968 |
| TF-mAb-H43 | 3302 | 2818 |
| TF-mAb-H44 | 3428 | 3195 |
| TF-mAb-H45 | 3478 | 3101 |
| TF-mAb-H46 | 3410 | 3115 |
| TF-mAb-H47 | 3151 | 2995 |
| TF-mAb-H48 | 2903 | 2611 |
| IgG (negative control) | 0 | 0 |

The effects of 9 humanized antibodies on the TF-PAR2 intracellular signal pathway were also determined. The experimental method is by referring to Example 4.

Figure 25:
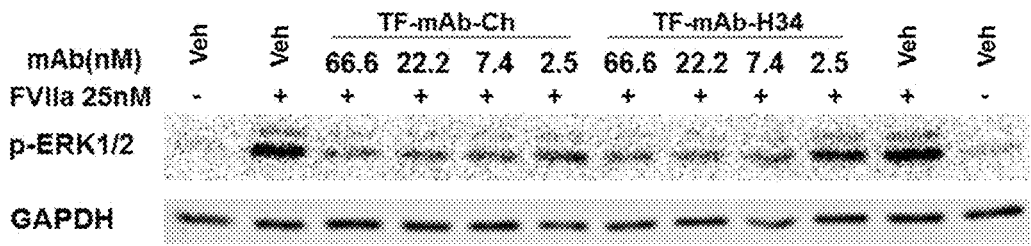
FIG. 25 shows the result on the effect of the humanized antibody on the TF-PAR2 intracellular signal pathway in BxPC-3 cells.
Figure 25:
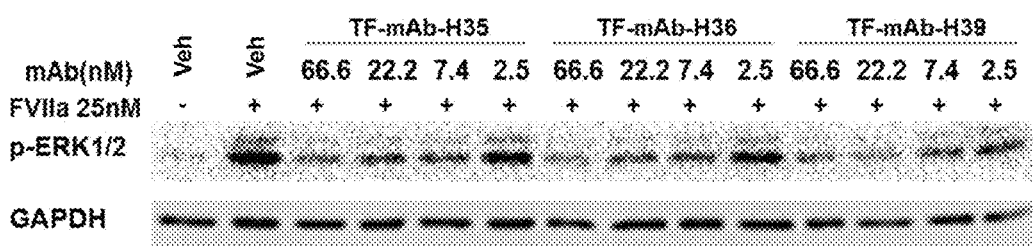
Figure 25:
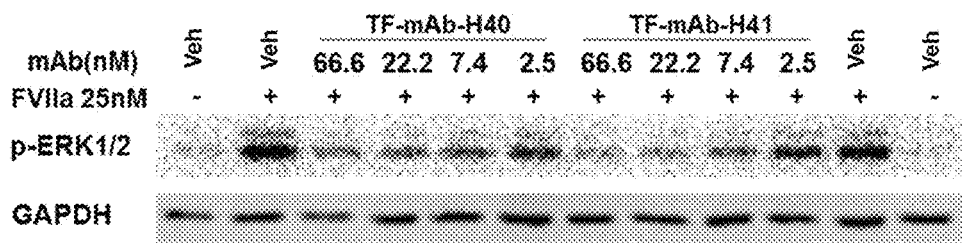
Figure 25:
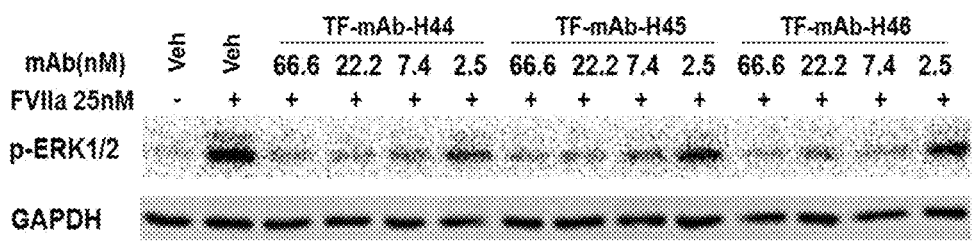

The experimental result shown in FIG. 25 indicated that each of the humanized antibodies inhibited the FVIIa-induced phosphorylation level of MAPK/ERK to a different extent in a concentration-dependent manner.

In addition, six humanized antibodies were determined for their inhibitory effect on tumor growth by in situ inoculation of nude mice at the mammary fatty pad with each of six humanized antibodies (100 μg for each antibody) after incubation with the tumor cells HCC1806. The experimental method is by referring to Example 7.

Figure 26:
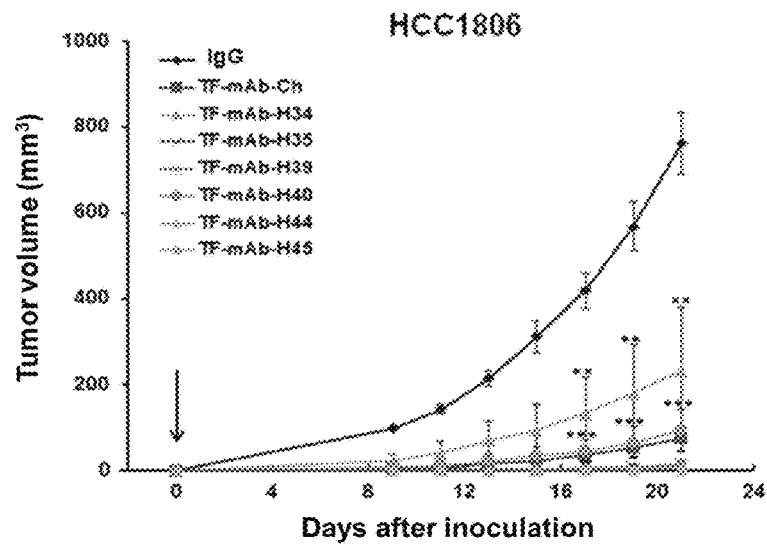
FIG. 26 shows the result on the activity of various humanized antibodies for inhibiting HCC1806 xenograft tumor growth.

The experimental result shown in FIG. 26 indicated that all the humanized antibodies showed a significant activity of inhibiting tumor growth, and among them, TF-mAb-H35, TF-mAb-H39, TF-mAb-H40, TF-mAb-H44 and TF-mAb-H45 exhibited an excellent activity of inhibiting tumor growth.

Figure 27:
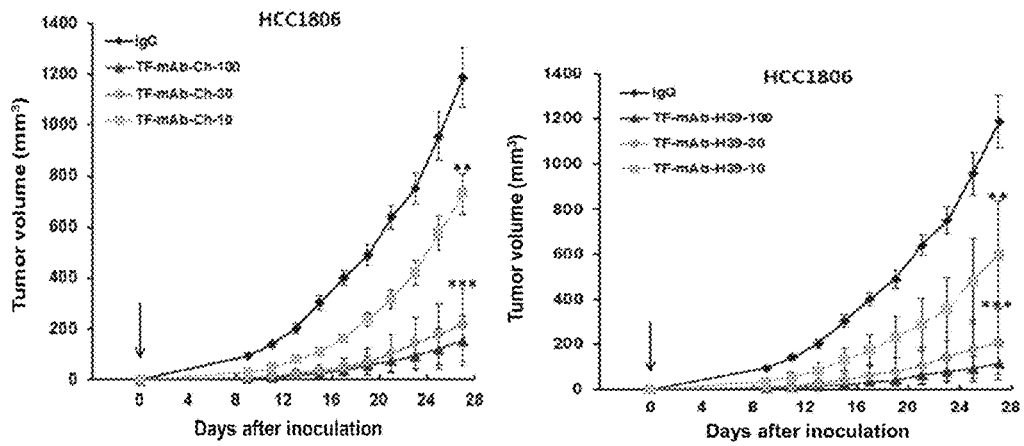
FIG. 27 shows the dose response activity of the chimeric antibody TF-mAb-Ch and the humanized antibody TF-mAb-H39 for inhibiting HCC1806 xenograft tumor growth.

In addition, the humanized antibody TF-mAb-H39 and the chimeric antibody TF-mAb-Ch were also determined for their effect of inhibiting the growth of HCC1806 xenografts by separate inoculation of nude mice at the mammary fatty pad with the humanized antibody TF-mAb-H39 and the chimeric antibody TF-mAb-Ch at a different dose (100 μg, 30 μg and 10 μg) after incubation with the tumor cells HCC1806. The experimental method is by referring to Example 7. The experimental results were shown in FIG. 27. The results showed that the humanized antibody TF-mAb-H39 had a tumor growth-inhibiting activity comparable to the activity of the chimeric antibody TF-mAb-Ch.

Example 18 Highly Abnormal Activation of TF in Basal-Like and Triple Negative Breast Cancer Firstly, the total cell protein was prepared for a variety of tumor cell lines derived from different tissues After accurate quantification, the expression level of TF protein was determined by Western blot.

Figure 28:
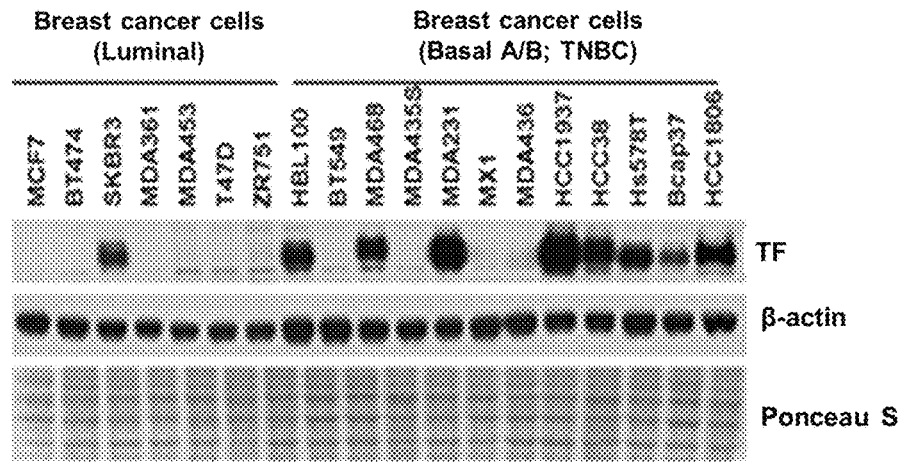
FIG. 28 shows the comparison of the expression results of TF protein in high-invasive and high-metastatic basal-like breast cancer (particularly triple-negative breast cancer) cell lines and in luminal subtype breast cancer cell line, as determined by Western blot.

The result showed that highly abnormal activation and expression of TF protein was present in some high-invasive and high-metastatic basal-like or basal A/B and triple-negative breast cancer (as shown in FIG. 28) cell lines; however, the high expression of TF protein only occurred in the cell lines of few luminal breast cancers with a low degree of malignancy.

Figure 29:
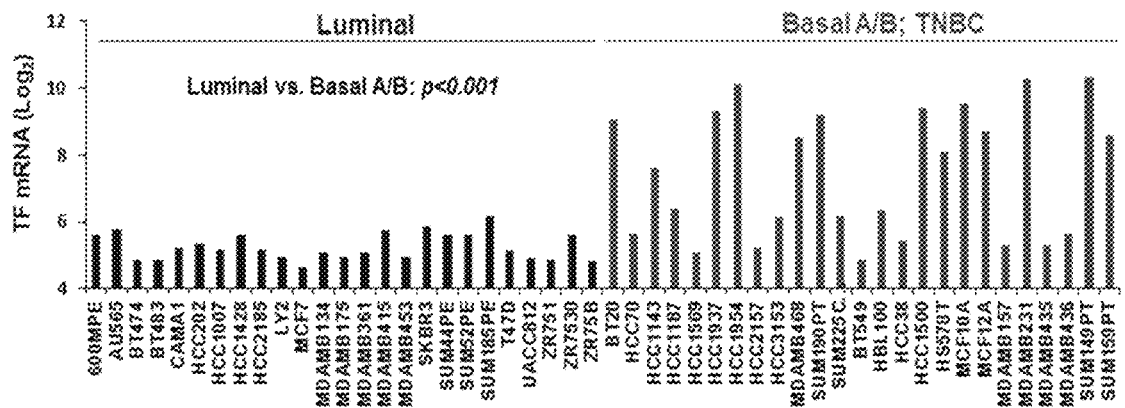
FIG. 29 shows the results of expression level comparison of TF mRNA in high-invasive and high-metastatic basal-like breast cancer (particularly triple-negative breast cancer) cell lines and in luminal subtype breast cancer cell line, as analyzed according to the database E-TABM-157 (European Molecular Biology Laboratory-European Bioinformatics Institute, EMBL-EBI).

Then, the expression level of TF mRNA in the breast cancer cell line in the database E-TABM-157 (European Molecular Biology Laboratory-European Bioinformatics Institute, EMBL-EBI) was analyzed. The results showed that the expression level of TF mRNA in the high-invasive and high-metastatic basal A/B and triple-negative breast cancer (especially triple-negative breast cancer) cell lines were generally higher than that in the luminal-subtype breast cancer cell lines, which was of statistical significance (FIG. 29). Therefore, the antibody targeted to TF according to the present invention had a more remarkable effect in the diagnosis, prevention and treatment of triple-negative breast cancer.

Example 19 Highly Abnormal Activation of TF in Pancreatic Cancer

Figure 30:
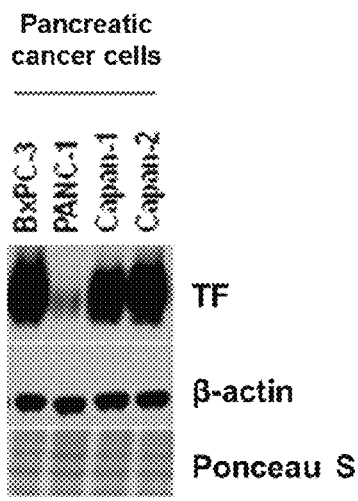
FIG. 30 shows the TF protein levels in different pancreatic cancer cell lines as determined by Western blot.
Figure 31:
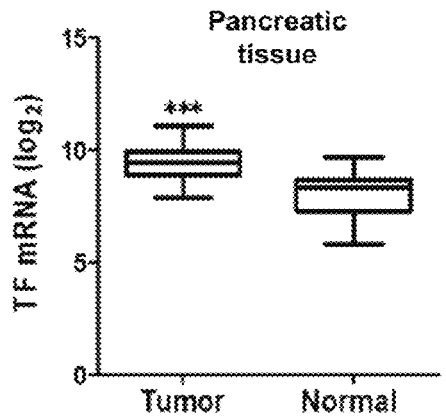
FIG. 31 shows the abnormal activation of TF mRNA in pancreatic cancer tissues compared with the adjacent normal tissues, as analyzed according to the database GSE15471 (Gene Expression Omnibus, GEO).

Firstly, the total cell protein was prepared for a variety of tumor cell lines derived from different tissues. After accurate quantification, the expression level of TF protein was determined by Western blot. The result showed that highly abnormal activation and expression of TF protein was present in high-invasive and high-metastatic pancreatic cancer (as shown in FIG. 30) cell lines, Then, the expression level of TF mRNA in pancreatic tumors and normal tissues in the database GSE15471 (Gene Expression Omnibus, GEO) was analyzed. The results showed that TF mRNA was generally expressed at a high level in pancreatic tumor tissues (FIG. 31). Therefore, the TF-targeting antibody according to the present invention had a more remarkable effect in the diagnosis, prevention and treatment of pancreatic cancer.

All the documents mentioned in the present invention are incorporated in the present application by reference to the same extent as if each individual document is specifically and individually indicated to be incorporated by reference. In addition, it should be understood that after reading the contents taught in the present invention, various modifications and changes may be made to the present invention by those skilled in the art, and these equivalents also fall into the scope defined by the claims.

The invention claimed is:

1. An anti-human tissue factor monoclonal antibody or an antigen-binding fragment thereof, wherein said antibody has
    a heavy chain variable region comprising HCDR1 as set forth in SEQ ID NO: 1, HCDR2 as set forth in SEQ ID NO: 2, and HCDR3 as set forth in SEQ ID NO: 3, and
    a light chain variable region comprising LCDR1 as set forth in SEQ ID NO: 4, LCDR2 as set forth in SEQ ID NO: 5, and LCDR3 as set forth in SEQ ID NO: 6.

2. The antibody according to claim 1, wherein the antibody is an animal-derived antibody, a chimeric antibody, or a humanized antibody.

3. The antibody according to claim 1, wherein the heavy chain variable region sequence of the antibody is selected from the group consisting of SEQ ID NOS: 7, 9, 10, 11, 12, and 13; and/or
    the light chain variable region sequence of the antibody is selected from the group consisting of SEQ ID NOS: 8, 14, 15, 16, and 17.

4. A method for treating cancer or a thrombotic disease, comprising administering a therapeutically effective amount of an anti-human tissue factor monoclonal antibody selected from the group consisting of TF-mAb-SC1, TF-mAb-Ch, TF-mAb-H29, TF-mAb-H30, TF-mAb-H31, TF-mAb-H32, TF-mAb-H33, TF-mAb-H34, TF-mAb-H35, TF-mAb-H36, TF-mAb-H37, TF-mAb-H38, TF-mAb-H39, TF-mAb-H40, TF-mAb-H41, TF-mAb-H42, TF-mAb-H43, TF-mAb-H44, TF-mAb-H45, TF-mAb-H46, TF-mAb-H47, and TF-mAb-H48 to a subject in need thereof.

5. The method according to claim 4, wherein the method is for treating a thrombotic disease.

6. The method according to claim 4, wherein the method is for treating cancer, and wherein the cancer is a cancer with high TF expression.

7. An isolated polynucleotide, which comprises a nucleic acid molecule encoding the heavy chain variable region of an anti-human tissue factor monoclonal antibody, and a nucleic acid molecule encoding the light chain variable region of said monoclonal antibody, wherein:
    the heavy chain variable region of the antibody comprises HCDR1 as set forth in SEQ ID NO: 1, HCDR2 as set forth in SEQ ID NO: 2, and HCDR3 as set forth in SEQ ID NO: 3, and
    the light chain variable region of the antibody comprises LCDR1 as set forth in SEQ ID NO: 4, LCDR2 as set forth in SEQ ID NO: 5, and LCDR3 as set forth in SEQ ID NO: 6.

8. A vector, comprising the isolated polynucleotide according to claim 7.

9. A genetically engineered host cell, comprising the vector according to claim 8.

10. An immune cell, wherein the immune cell expresses the antibody according to claim 1.

11. A pharmaceutical composition, comprising the antibody according to claim 1 and a pharmaceutically acceptable carrier.

12. A method for determining the presence or absence of a TF protein in a sample in vitro, the method comprises:
    (1) contacting the sample with the antibody according to claim 1 in vitro; and
    (2) determining whether an antigen-antibody complex is formed, wherein the formation of the complex indicates the presence of a TF protein in the sample.

13. A method for preparing an anti-human tissue factor monoclonal antibody, comprising:
    (a) culturing the host cell according to claim 9 under conditions suitable for expressing an anti-human tissue factor monoclonal antibody; and
    (b) separating the antibody from the culture.

14. The antibody according to claim 3, wherein the antibody is selected from the group consisting of: TF-mAb-SC1, TF-mAb-Ch, TF-mAb-H29, TF-mAb-H30, TF-mAb-H31, TF-mAb-H32, TF-mAb-H33, TF-mAb-H34, TF-mAb-H35, TF-mAb-H36, TF-mAb-H37, TF-mAb-H38, TF-mAb-H39, TF-mAb-H40, TF-mAb-H41, TF-mAb-H42, TF-mAb-H43, TF-mAb-H44, TF-mAb-H45, TF-mAb-H46, TF-mAb-H47, and TF-mAb-H48.

15. The antibody according to claim 1, wherein the antibody has an EC50 of 0.01-0.03 nM for the affinity to human TF protein.

16. The isolated polynucleotide according to claim 7, wherein:
    the heavy chain variable region sequence of the antibody is SEQ ID NO: 7, 9, 10, 11, 12, or 13; and/or
    the light chain variable region sequence of the antibody is SEQ ID NO: 8, 14, 15, 16, or 17.

17. The isolated polynucleotide according to claim 7, wherein the antibody is selected from the group consisting of: TF-mAb-SC1, TF-mAb-Ch, TF-mAb-H29, TF-mAb-H30, TF-mAb-H31, TF-mAb-H32, TF-mAb-H33, TF-mAb-H34, TF-mAb-H35, TF-mAb-H36, TF-mAb-H37, TF-mAb-H38, TF-mAb-H39, TF-mAb-H40, TF-mAb-H41, TF-mAb-H42, TF-mAb-H43, TF-mAb-H44, TF-mAb-H45, TF-mAb-H46, TF-mAb-H47, and TF-mAb-H48.

* * * * *

```
                        SEQUENCE LISTING

<160> NUMBER OF SEQ ID NOS: 23

<210> SEQ ID NO 1
<211> LENGTH: 5
<212> TYPE: PRT
<213> ORGANISM: Mus musculus

<400> SEQUENCE: 1

Ser Tyr Trp Met Asn
1               5

<210> SEQ ID NO 2
<211> LENGTH: 17
<212> TYPE: PRT
<213> ORGANISM: Mus musculus

<400> SEQUENCE: 2

Met Ile Tyr Pro Ala Asp Ser Glu Thr Arg Leu Asn Gln Lys Phe Lys
1               5                   10                  15

Asp

<210> SEQ ID NO 3
<211> LENGTH: 8
<212> TYPE: PRT
<213> ORGANISM: Mus musculus

<400> SEQUENCE: 3

Glu Asp Tyr Gly Ser Ser Asp Tyr
1               5

<210> SEQ ID NO 4
<211> LENGTH: 10
<212> TYPE: PRT
<213> ORGANISM: Mus musculus

<400> SEQUENCE: 4

Ser Ala Ser Ser Ser Val Ser Tyr Met Asn
1               5                   10

<210> SEQ ID NO 5
<211> LENGTH: 7
<212> TYPE: PRT
```

```
<213> ORGANISM: Mus musculus

<400> SEQUENCE: 5

Gly Ile Ser Asn Leu Ala Ser
1               5

<210> SEQ ID NO 6
<211> LENGTH: 9
<212> TYPE: PRT
<213> ORGANISM: Mus musculus

<400> SEQUENCE: 6

Gln Gln Lys Ser Ser Phe Pro Trp Thr
1               5

<210> SEQ ID NO 7
<211> LENGTH: 117
<212> TYPE: PRT
<213> ORGANISM: Mus musculus

<400> SEQUENCE: 7

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Ser Phe Ile Ser Tyr
            20                  25                  30

Trp Met Asn Trp Val Lys Gln Arg Pro Gly Gln Gly Leu Glu Trp Ile
        35                  40                  45

Gly Met Ile Tyr Pro Ala Asp Ser Glu Thr Arg Leu Asn Gln Lys Phe
    50                  55                  60

Lys Asp Lys Ala Thr Leu Thr Val Asp Lys Ser Ser Thr Ala Tyr
65                  70                  75                  80

Met Gln Leu Ser Ser Pro Thr Ser Glu Asp Ser Ala Val Tyr Tyr Cys
                85                  90                  95

Ala Arg Glu Asp Tyr Gly Ser Ser Asp Tyr Trp Gly Gln Gly Thr Thr
            100                 105                 110

Leu Thr Val Ser Ser
        115

<210> SEQ ID NO 8
<211> LENGTH: 106
<212> TYPE: PRT
<213> ORGANISM: Mus musculus

<400> SEQUENCE: 8

Glu Ile Leu Leu Thr Gln Ser Pro Ala Ile Ala Ala Ser Pro Gly
1               5                   10                  15

Glu Lys Val Thr Ile Thr Cys Ser Ala Ser Ser Val Ser Tyr Met
            20                  25                  30

Asn Trp Tyr Leu Gln Lys Pro Gly Ser Ser Pro Lys Ile Trp Ile Tyr
        35                  40                  45

Gly Ile Ser Asn Leu Ala Ser Gly Val Pro Ala Arg Phe Ser Gly Ser
    50                  55                  60

Gly Ser Gly Thr Ser Phe Ser Phe Thr Ile Asn Ser Met Glu Thr Glu
65                  70                  75                  80

Asp Val Ala Thr Tyr Tyr Cys Gln Gln Lys Ser Ser Phe Pro Trp Thr
                85                  90                  95

Phe Gly Gly Gly Thr Lys Leu Glu Ile Lys
            100                 105
```

<210> SEQ ID NO 9
<211> LENGTH: 117
<212> TYPE: PRT
<213> ORGANISM: Artificial sequence
<220> FEATURE:
<223> OTHER INFORMATION: VH

<400> SEQUENCE: 9

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Met Asn Trp Val Arg Gln Met Pro Gly Lys Gly Leu Glu Trp Met
        35                  40                  45

Gly Met Ile Tyr Pro Ala Asp Ser Glu Thr Arg Leu Asn Gln Lys Phe
    50                  55                  60

Lys Asp Gln Ala Thr Leu Ser Val Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Glu Asp Tyr Gly Ser Ser Asp Tyr Trp Gly Gln Gly Thr Thr
            100                 105                 110

Val Thr Val Ser Ser
        115
```

<210> SEQ ID NO 10
<211> LENGTH: 117
<212> TYPE: PRT
<213> ORGANISM: Artificial sequence
<220> FEATURE:
<223> OTHER INFORMATION: VH

<400> SEQUENCE: 10

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Met Asn Trp Val Arg Gln Met Pro Gly Lys Gly Leu Glu Trp Met
        35                  40                  45

Gly Met Ile Tyr Pro Ala Asp Ser Glu Thr Arg Leu Asn Gln Lys Phe
    50                  55                  60

Lys Asp Lys Ala Thr Leu Ser Val Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Glu Asp Tyr Gly Ser Ser Asp Tyr Trp Gly Gln Gly Thr Thr
            100                 105                 110

Val Thr Val Ser Ser
        115
```

<210> SEQ ID NO 11
<211> LENGTH: 117
<212> TYPE: PRT
<213> ORGANISM: Artificial sequence
<220> FEATURE:
<223> OTHER INFORMATION: VH

<400> SEQUENCE: 11

```
Glu Val Gln Leu Val Gln Ser Gly Ala Glu Val Lys Lys Pro Gly Glu
```

```
                1               5                   10                  15
Ser Leu Lys Ile Ser Cys Lys Gly Ser Gly Tyr Ser Phe Thr Ser Tyr
                20                  25                  30

Trp Met Asn Trp Val Lys Gln Met Pro Gly Lys Gly Leu Glu Trp Met
        35                  40                  45

Gly Met Ile Tyr Pro Ala Asp Ser Glu Thr Arg Leu Asn Gln Lys Phe
        50                  55                  60

Lys Asp Lys Ala Thr Leu Ser Val Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Glu Asp Tyr Gly Ser Ser Asp Tyr Trp Gly Gln Gly Thr Thr
                100                 105                 110

Val Thr Val Ser Ser
        115

<210> SEQ ID NO 12
<211> LENGTH: 117
<212> TYPE: PRT
<213> ORGANISM: Artificial sequence
<220> FEATURE:
<223> OTHER INFORMATION: VH

<400> SEQUENCE: 12

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Ile Ser Tyr
                20                  25                  30

Trp Met Asn Trp Val Arg Gln Ala Pro Gly Gln Gly Leu Glu Trp Ile
        35                  40                  45

Gly Met Ile Tyr Pro Ala Asp Ser Glu Thr Arg Leu Asn Gln Lys Phe
        50                  55                  60

Lys Asp Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Asp Tyr Gly Ser Ser Asp Tyr Trp Gly Gln Gly Thr Thr
                100                 105                 110

Val Thr Val Ser Ser
        115

<210> SEQ ID NO 13
<211> LENGTH: 117
<212> TYPE: PRT
<213> ORGANISM: Artificial sequence
<220> FEATURE:
<223> OTHER INFORMATION: VH

<400> SEQUENCE: 13

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Ser Phe Ile Ser Tyr
                20                  25                  30

Trp Met Asn Trp Val Arg Gln Ala Pro Gly Gln Gly Leu Glu Trp Ile
        35                  40                  45

Gly Met Ile Tyr Pro Ala Asp Ser Glu Thr Arg Leu Asn Gln Lys Phe
        50                  55                  60
```

```
Lys Asp Arg Ala Val Leu Ser Val Asp Lys Ser Val Ser Thr Ala Tyr
 65                  70                  75                  80

Leu Gln Ile Cys Ser Leu Lys Ala Glu Asp Thr Ala Val Tyr Tyr Cys
                 85                  90                  95

Ala Arg Glu Asp Tyr Gly Ser Ser Asp Tyr Trp Gly Gln Gly Thr Thr
            100                 105                 110

Val Thr Val Ser Ser
        115
```

```
<210> SEQ ID NO 14
<211> LENGTH: 106
<212> TYPE: PRT
<213> ORGANISM: Artificial sequence
<220> FEATURE:
<223> OTHER INFORMATION: VL

<400> SEQUENCE: 14

Glu Ile Val Leu Thr Gln Ser Pro Ala Thr Leu Ser Leu Ser Pro Gly
 1               5                  10                  15

Glu Arg Ala Thr Leu Ser Cys Ser Ala Ser Ser Ser Val Ser Tyr Met
             20                  25                  30

Asn Trp Tyr Gln Gln Lys Pro Gly Gln Ala Pro Arg Ile Trp Ile Tyr
         35                  40                  45

Gly Ile Ser Asn Leu Ala Ser Gly Ile Pro Ala Arg Phe Ser Gly Ser
     50                  55                  60

Gly Ser Gly Thr Asp Phe Thr Leu Thr Ile Ser Ser Leu Glu Pro Glu
 65                  70                  75                  80

Asp Phe Ala Val Tyr Tyr Cys Gln Gln Lys Ser Ser Phe Pro Trp Thr
                 85                  90                  95

Phe Gly Gly Gly Thr Lys Val Glu Ile Lys
            100                 105
```

```
<210> SEQ ID NO 15
<211> LENGTH: 106
<212> TYPE: PRT
<213> ORGANISM: Artificial sequence
<220> FEATURE:
<223> OTHER INFORMATION: VL

<400> SEQUENCE: 15

Glu Ile Val Leu Thr Gln Ser Pro Ala Thr Leu Ser Leu Ser Pro Gly
 1               5                  10                  15

Glu Arg Ala Thr Leu Ser Cys Ser Ala Ser Ser Ser Val Ser Tyr Met
             20                  25                  30

Asn Trp Tyr Gln Gln Lys Pro Gly Gln Ser Pro Arg Ile Trp Ile Tyr
         35                  40                  45

Gly Ile Ser Asn Leu Ala Ser Gly Val Pro Ala Arg Phe Ser Gly Ser
     50                  55                  60

Gly Ser Gly Thr Asp Phe Thr Leu Thr Ile Ser Ser Leu Glu Pro Glu
 65                  70                  75                  80

Asp Phe Ala Val Tyr Tyr Cys Gln Gln Lys Ser Ser Phe Pro Trp Thr
                 85                  90                  95

Phe Gly Gly Gly Thr Lys Val Glu Ile Lys
            100                 105
```

```
<210> SEQ ID NO 16
<211> LENGTH: 106
<212> TYPE: PRT
<213> ORGANISM: Artificial sequence
```

<220> FEATURE:
<223> OTHER INFORMATION: VL

<400> SEQUENCE: 16

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ser Val Ser Tyr Met
            20                  25                  30

Asn Trp Tyr Gln Gln Lys Pro Gly Lys Ser Pro Lys Ile Trp Ile Tyr
        35                  40                  45

Gly Ile Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Lys Ser Ser Phe Pro Trp Thr
                85                  90                  95

Phe Gly Gly Gly Thr Lys Val Glu Ile Lys
            100                 105

<210> SEQ ID NO 17
<211> LENGTH: 106
<212> TYPE: PRT
<213> ORGANISM: Artificial Seugence
<220> FEATURE:
<223> OTHER INFORMATION: VL

<400> SEQUENCE: 17

Glu Ile Val Leu Thr Gln Ser Pro Asp Phe Gln Ser Val Thr Pro Lys
1               5                   10                  15

Glu Lys Val Thr Ile Thr Cys Ser Ala Ser Ser Val Ser Tyr Met
            20                  25                  30

Asn Trp Tyr Gln Gln Lys Pro Asp Gln Ser Pro Lys Ile Trp Ile Tyr
        35                  40                  45

Gly Ile Ser Asn Leu Ala Ser Gly Val Pro Ser Arg Phe Ser Gly Ser
    50                  55                  60

Gly Ser Gly Thr Asp Phe Thr Leu Thr Ile Asn Ser Leu Glu Ala Glu
65                  70                  75                  80

Asp Ala Ala Thr Tyr Tyr Cys Gln Gln Lys Ser Ser Phe Pro Trp Thr
                85                  90                  95

Phe Gly Gly Gly Thr Lys Val Glu Ile Lys
            100                 105

<210> SEQ ID NO 18
<211> LENGTH: 17
<212> TYPE: PRT
<213> ORGANISM: Artificial sequence
<220> FEATURE:
<223> OTHER INFORMATION: CDR
<220> FEATURE:
<221> NAME/KEY: MISC_FEATURE
<222> LOCATION: (5)..(5)
<223> OTHER INFORMATION: Xaa=A, D, E, Q or Y
<220> FEATURE:
<221> NAME/KEY: MISC_FEATURE
<222> LOCATION: (13)..(13)
<223> OTHER INFORMATION: Xaa=A, D, E, Q or Y

<400> SEQUENCE: 18

Met Ile Tyr Pro Xaa Asp Ser Glu Thr Arg Leu Asn Xaa Lys Phe Lys
1               5                   10                  15

Asp

```
<210> SEQ ID NO 19
<211> LENGTH: 10
<212> TYPE: PRT
<213> ORGANISM: Artificial sequence
<220> FEATURE:
<223> OTHER INFORMATION: CDR
<220> FEATURE:
<221> NAME/KEY: MISC_FEATURE
<222> LOCATION: (5)..(5)
<223> OTHER INFORMATION: Xaa=A, I, Y, Q or W

<400> SEQUENCE: 19

Gly Tyr Ser Phe Xaa Ser Tyr Trp Met Asn
1               5                   10

<210> SEQ ID NO 20
<211> LENGTH: 10
<212> TYPE: PRT
<213> ORGANISM: Artificial sequence
<220> FEATURE:
<223> OTHER INFORMATION: CDR
<220> FEATURE:
<221> NAME/KEY: MISC_FEATURE
<222> LOCATION: (7)..(7)
<223> OTHER INFORMATION: Xaa=S, P, G, D, M or N

<400> SEQUENCE: 20

Ala Arg Glu Asp Tyr Gly Xaa Ser Asp Tyr
1               5                   10

<210> SEQ ID NO 21
<211> LENGTH: 9
<212> TYPE: PRT
<213> ORGANISM: Artificial sequence
<220> FEATURE:
<223> OTHER INFORMATION: CDR
<220> FEATURE:
<221> NAME/KEY: MISC_FEATURE
<222> LOCATION: (3)..(3)
<223> OTHER INFORMATION: Xaa= S, P, K, G or H
<220> FEATURE:
<221> NAME/KEY: MISC_FEATURE
<222> LOCATION: (7)..(7)
<223> OTHER INFORMATION: Xaa= S, P, K, G or H

<400> SEQUENCE: 21

Gln Gln Xaa Ser Ser Phe Xaa Trp Thr
1               5

<210> SEQ ID NO 22
<211> LENGTH: 10
<212> TYPE: PRT
<213> ORGANISM: Artificial sequence
<220> FEATURE:
<223> OTHER INFORMATION: CDR
<220> FEATURE:
<221> NAME/KEY: MISC_FEATURE
<222> LOCATION: (5)..(5)
<223> OTHER INFORMATION: Xaa=A, P, D or S

<400> SEQUENCE: 22

Ser Ala Ser Ser Xaa Val Ser Tyr Met Asn
1               5                   10

<210> SEQ ID NO 23
<211> LENGTH: 7
<212> TYPE: PRT
<213> ORGANISM: Artificial sequence
<220> FEATURE:
```

```
<223> OTHER INFORMATION: CDR
<220> FEATURE:
<221> NAME/KEY: MISC_FEATURE
<222> LOCATION: (2)..(2)
<223> OTHER INFORMATION: Xaa=P, D, I or S

<400> SEQUENCE: 23

Gly Xaa Ser Asn Leu Ala Ser
1               5
```